US 9,987,333 B2

(12) United States Patent
Kangawa et al.

(10) Patent No.: US 9,987,333 B2
(45) Date of Patent: Jun. 5, 2018

(54) METHOD FOR SUPPRESSING MALIGNANT TUMOR METASTASIS

(71) Applicants: Shionogi & Co., Ltd., Osaka (JP); National Cerebral and Cardiovascular Center, Osaka (JP)

(72) Inventors: Kenji Kangawa, Osaka (JP); Hiroshi Hosoda, Osaka (JP); Takashi Nojiri, Osaka (JP)

(73) Assignees: Shionogi & Co., Ltd., Osaka (JP); National Cerebral and Cardiovascular Center, Osaka (JP)

( * ) Notice: Subject to any disclaimer, the term of this patent is extended or adjusted under 35 U.S.C. 154(b) by 0 days. days.

(21) Appl. No.: 15/270,669

(22) Filed: Sep. 20, 2016

(65) Prior Publication Data
US 2017/0035855 A1 Feb. 9, 2017

Related U.S. Application Data

(63) Continuation of application No. 14/433,149, filed as application No. PCT/JP2013/077140 on Oct. 4, 2013, now Pat. No. 9,486,503.

(30) Foreign Application Priority Data

Oct. 4, 2012 (JP) ................................. 2012-221795

(51) Int. Cl.

| A61K 38/25 | (2006.01) |
|---|---|
| A61K 31/41 | (2006.01) |
| A61K 38/22 | (2006.01) |
| A61K 45/06 | (2006.01) |
| A61K 31/4184 | (2006.01) |
| A61K 31/47 | (2006.01) |
| A61K 33/24 | (2006.01) |
| A61K 31/4178 | (2006.01) |
| A61K 31/4245 | (2006.01) |
| A61K 31/555 | (2006.01) |
| A61K 31/473 | (2006.01) |

(52) U.S. Cl.
CPC .............. *A61K 38/25* (2013.01); *A61K 31/41* (2013.01); *A61K 31/4178* (2013.01); *A61K 31/4184* (2013.01); *A61K 31/4245* (2013.01); *A61K 31/47* (2013.01); *A61K 31/473* (2013.01); *A61K 31/555* (2013.01); *A61K 33/24* (2013.01); *A61K 38/22* (2013.01); *A61K 45/06* (2013.01)

(58) Field of Classification Search
None
See application file for complete search history.

(56) References Cited

U.S. PATENT DOCUMENTS

| 4,231,938 A | 11/1980 | Monaghan et al. |
|---|---|---|
| 4,444,784 A | 4/1984 | Hoffman et al. |
| 5,616,599 A | 4/1997 | Yanagisawa et al. |
| 5,646,171 A | 7/1997 | Yanagisawa et al. |
| 6,320,022 B1 | 11/2001 | Cutitta et al. |
| 7,385,026 B1 | 6/2008 | Kangawa et al. |
| 8,227,570 B2 | 7/2012 | Kangawa et al. |
| 8,524,871 B2 | 9/2013 | Kangawa et al. |
| 2005/0119323 A1 | 6/2005 | Kubota et al. |
| 2005/0209292 A1 | 9/2005 | Chuang et al. |
| 2006/0160730 A1 | 7/2006 | Cuttitta et al. |
| 2006/0241122 A1 | 10/2006 | Lee et al. |
| 2006/0264384 A1 | 11/2006 | Johansen et al. |
| 2007/0037751 A1 | 2/2007 | Lange et al. |
| 2008/0171700 A1 | 7/2008 | Nilsson et al. |
| 2009/0048170 A1 | 2/2009 | Cuttitta et al. |
| 2009/0082406 A1 | 3/2009 | Chuang et al. |
| 2010/0240866 A1 | 9/2010 | Kangawa et al. |
| 2011/0189205 A1 | 8/2011 | Dickerson et al. |
| 2011/0262423 A1 | 10/2011 | Madec et al. |
| 2013/0172251 A1 | 7/2013 | Kangawa et al. |
| 2014/0072557 A1 | 3/2014 | Kangawa et al. |

FOREIGN PATENT DOCUMENTS

| EP | 0459136 A1 | 12/1991 |
|---|---|---|
| EP | 0720982 A1 | 7/1996 |
| GB | 2202846 A | 10/1988 |
| JP | S 59-48418 | 3/1984 |
| JP | H 04364171 A | 12/1992 |
| JP | H 0578328 | 3/1993 |
| JP | 2005-200419 A | 7/2005 |
| JP | 2006-526640 A | 11/2006 |
| JP | 2007-523048 A | 8/2007 |
| JP | 2008-540455 A | 11/2008 |
| JP | 2009-523778 A | 6/2009 |
| WO | 01/07475 A1 | 2/2001 |
| WO | 2007/083119 A2 | 7/2007 |
| WO | 2011/047383 A1 | 4/2011 |
| WO | 2012/118042 A1 | 9/2012 |

*Primary Examiner* — Elly-Gerald Stoica
(74) *Attorney, Agent, or Firm* — Mintz Levin Cohn Ferris Glovsky and Popeo, P.C.; David G. Conlin; Joohee Lee

(57) ABSTRACT

A medicinal composition for suppressing or preventing the metastasis of a malignant tumor, the composition comprising, as an active ingredient, at least one kind of vasoprotective agent selected from the following (i) to (iv): (i) angiotensin II receptor antagonist, (ii) HMG-CoA reductase inhibitor, (iii) ghrelin or its derivative, and (iv) adrenomedullin or its derivative; or a pharmacologically acceptable salt thereof.

10 Claims, 6 Drawing Sheets

A Control group    B CDDP group    C Adrenomedullin group    D Ghrelin group

METHOD FOR SUPPRESSING MALIGNANT TUMOR METASTASIS

CROSS REFERENCE TO RELATED APPLICATION

The present application is a continuation application of U.S. patent application Ser. No. 14/433,149 filed Apr. 2, 2015, which is a National Stage Entry of International Patent Application No. PCT/JP2013/077140 filed Oct. 4, 2013, which also claims priority to Japanese Patent Application No 2012-221795, filed Oct. 4, 2012. The entire contents of these applications are incorporated herein for all purposes by this reference.

INCORPORATION-BY-REFERENCE OF A SEQUENCE LISTING

The sequence listing contained in the file "48669-516C01US_Sequence_Listing.txt", created on 2016 Sep. 20, file size 10,532 bytes, is incorporated by reference in its entirety herein.

TECHNICAL FIELD

The present invention relates to a novel medicinal composition for suppressing or preventing the metastasis of a malignant tumor, such as carcinoma, the agent comprising, as an active ingredient, a vasoprotective agent. The present invention also relates to a novel treatment or prevention method etc. for suppressing or preventing the metastasis of a malignant tumor. The present invention further relates to a medicinal composition for suppressing or preventing malignant tumor cells from colonizing or invading vascular endothelium, and also relates to a method for suppressing or preventing malignant tumor cells from colonizing or invading vascular endothelium.

BACKGROUND ART

Malignant tumors represented by carcinoma are diseases caused by abnormal growth of cells, and the most distinctive characteristic of malignant tumors is invasion into the surrounding tissue and metastasis to other organs. It has been long known that the leading cause of death for malignant tumor patients is not the growth of the primary lesion but multiple organ failure resulting from distant metastasis of the tumor cells. However, control of malignant tumor metastasis has not yet been achieved so far and is one of the most crucial issues in the whole area of cancer treatment.

Metastasis of an epithelial malignant tumor (carcinoma) is considered to be caused by various physiological phenomena of cancer cells, such as the acquisition of motility and migrating ability typified by epithelial to mesenchymal transition (hereinafter, abbreviated to "EMT"), invasion into the surrounding tissue, migration and invasion into blood vessels and lymphatic vessels, colonization in vascular endothelium of distant tissue, metastatic lesion formation, etc.

Also in a non-epithelial malignant tumor (sarcoma etc.), tumor cells that have become malignant and acquired motility and migrating ability invade blood vessels etc., colonize vascular endothelium of distant tissue, invade the tissue, and then form a metastatic lesion.

In this process, interaction between endothelial selectins of blood vessels, in particular capillary vessels, and selectin ligands expressed on tumor cells is involved in the colonization of circulating tumor cells in vascular endothelium (Non Patent Literature 1). It is also known that inflammatory cytokines (IL-1β, TNF-α) promote the adhesion of tumor cells to vascular endothelium (Non Patent Literature 2 and 3). For example, inflammatory cytokines produced by surgery or a surgery-induced infection systemically and locally promote the adhesion of tumor cells to vascular endothelium and facilitate the metastasis of the tumor cells to distant tissue and tumor recurrence at the primary site (Non Patent Literature 1 to 3).

In the prevailing pharmacological treatment for cancer, an anticancer/antitumor agent is administered to a tumor-bearing patient usually for the purpose of reducing the size of the primary focus, and the effect of the anticancer/antitumor agent is judged by the reduction percentage. However, an anticancer/antitumor agent is often harmful to normal tissue, and so-called "adverse effects" that cause various organ disorders appear at a high rate. Therefore, chronic dosing thereof causes problems of such serious side effects. For this reason, in actual cancer treatment, the administration of anticancer/antitumor agents has often to be restricted in terms of the amount and duration, leading to shortened life expectancy.

Ghrelin is a hormone found in the stomach in 1999. For example, the ghrelin of a mammal, such as a human, is a peptide having an amino acid sequence composed of 28 residues and having an extremely rare chemical structure in which the 3rd amino acid from the N terminus in the sequence is acylated with a fatty acid (Non Patent Literature 4 and Patent Literature 1).

Ghrelin is an endogenous cerebral-gastrointestinal hormone that acts on a growth hormone secretagogue-receptor 1a (GHS-R1a) and thereby promotes secretion of a growth hormone (GH) from the pituitary (Non Patent Literature 4 and 5).

Recent studies have revealed that ghrelin increases appetite, that subcutaneous administration of ghrelin increases body weight and body fat, and that ghrelin has activities such as improvement of cardiac function (Non Patent Literature 6 to 10). Further, since ghrelin has GH secretion promoting activity and appetite stimulation activity, it is expected that ghrelin, through the activity of GH, further effectively exerts fat-burning activity for converting fat into energy and the effect of strengthening muscles through the anabolic activity of GH (Non Patent Literature 11).

Adrenomedullin (hereinafter sometimes referred to as "AM") is a peptide having a strong vasodilating effect. It was first isolated from human pheochromocytoma, and later immunoreactive AM was detected in various tissues including lung tissue (Non Patent Literature 12 to 14). AM receptor expression is abundant in the basal cells of the airway epithelium and Type II pneumocytes, and the two cell types are involved in epithelial regeneration of the lung (Non Patent Literature 15). In recent studies, it has been shown that AM activates, in vascular endothelial cells, the phosphatidylinositol 3-kinase/Akt dependent pathway, which is considered to regulate many essential steps for cell growth (Non Patent Literature 16 to 19).

Angiotensin II has an effect of, via angiotensin II receptors on cell membrane, constricting blood vessels to raise blood pressure. Therefore, an angiotensin II receptor antagonist can be an effective treatment agent for circulatory diseases, such as hypertension. A known example of a preferable chemical structure which exhibits a strong angiotensin II antagonistic effect is a structure having a biphenyl group substituted with a tetrazolyl group, a carboxyl group, or the like on the side chain. Pharmaceutical compounds having such a structural feature, for example, losartan, candesartan cilexetil, olmesartan medoxomil, etc. are clinically used as a treatment agent for hypertension (Non Patent Literature 20, Patent Literature 2 and 3, etc.).

HMG-CoA (3-hydroxy-3-methyl-glutaryl-coenzyme A) reductase inhibitor specifically inhibits HMG-CoA reductase, which is a rate-limiting enzyme of biosynthesis of cholesterol. It is known that HMG-CoA reductase inhibitor, which suppresses the synthesis of cholesterol, is effective in the treatment of hypercholesterolemia, hyperlipoproteinemia, atherosclerosis, etc. (Non Patent Literature 21).

Known examples of the 1st generation of HMG-CoA reductase inhibitor include mevinolin, pravastatin, simvastatin, etc., which are a fungal metabolite or a partially modified product thereof (Patent Literature 4 to 6). After the emergence of the 1st generation drugs, synthetic HMG-CoA reductase inhibitors, such as fluvastatin, were developed, which are known as 2nd generation (Non Patent Literature 22 and Patent Literature 7).

However, it has been unknown that ghrelin, adrenomedullin, and HMG-CoA reductase inhibitors suppress the metastasis of malignant tumor cells (especially that they suppress the metastasis of a malignant tumor without targeting the malignant tumor itself).

Meanwhile, Non Patent Literature 23 describes, regarding angiotensin II receptor antagonists, that losartan suppressed the lung metastasis of renal cell carcinoma increased by cyclosporin (Cs). Non Patent Literature 24 describes that losartan suppressed the liver metastasis of colon cancer cells. Non Patent Literature 25 describes that candesartan suppressed the lung metastasis of renal cell carcinoma by inhibiting tumor angiogenesis and vascular endothelial growth factor (VEGF) expression. Non Patent Literature 26 describes that candesartan suppressed the lung and liver metastasis of osteosarcoma. Non Patent Literature 27 describes that candesartan cilexetil (TCV-116) suppressed the angiogenesis and metastasis of a tumor. Non Patent Literature 28 describes that angiotensin II type 1 receptor (AT1 receptor) system is involved in the growth, angiogenesis, and metastasis of a tumor.

Also, Non Patent Literature 29 describes that lovastatin as a HMG-CoA reductase inhibitor inhibits E select in expression and inhibits the adhesion of colon cancer cells to human umbilical vein endothelial cells (HUVECs).

Patent Literature 8 discloses medicines for suppressing or preventing the metastasis of a malignant tumor, the medicines comprising, as an active ingredient, vascular endothelial intracellular cGMP enhancers, such as natriuretic peptide receptor GC-A agonist, but does not disclose the effects of ghrelin, adrenomedullin, angiotensin II receptor antagonists, and HMG-CoA reductase inhibitors on the metastasis of a malignant tumor.

CITATION LIST

Patent Literature

PTL 1: WO 01/07475
PTL 2: JP-04-364171 A
PTL 3: JP-05-78328 A
PTL 4: U.S. Pat. No. 4,231,938
PTL 5: JP-59-48418 A
PTL 6: U.S. Pat. No. 4,444,784
PTL 7: GB Pat. No. 2,202,846
PTL 8: WO 2012/118042

Non Patent Literature

NPL 1: Braedon McDonald et al., Int. J. Cancer 125, 1298-1305 (2009)
NPL 2: Miranda Ten Kate et al., Int. J. Cancer 112, 943-950 (2004)
NPL 3: Ge Yu at al., Surg Endosc, 24, 2860-2870 (2010)
NPL 4: Kojima at al., Nature, 402, 656-660 (1999)
NPL 5: Howard at al., Science, 273, 974-977 (1996)
NPL 6: Wren at al., Endocrinology, 141, 4325-4328 (2000)
NPL 7: Nakazato at al., Nature, 409, 194-198 (2001)
NPL 8: Shintani at al., Diabetes, 50, 227-232 (2001)
NPL 9: Lely at al., Endocr. Rev., 25, 656-660 (2004)
NPL 10: Korbonits at al., Front Neuroendocrinol., 25, 27-68 (2004)
NPL 11: Kangawa at al., J. Pharmacol. Sci., 100, 398-410 (2006)
NPL 12: Kitamura K at al., Biochem Biophys Res Commun, 192, 553-560 (1993)
NPL 13: Ichiki Y at al., FEBS Lett, 338, 6-10 (1994)
NPL 14: Sakata J at al., FEBS Lett, 352, 105-108 (1994)
NPL 15: Martinez A at al., J Histochem Cytochem, 45, 159-164 (1997)
NPL 16: Nishimatsu H at al., Circ Res, 89(1), 63-70 (2001)
NPL 17: Shiojima I at al., 90, 1243-1250 (2002)
NPL 18: Kim W at al., FASEB J, 17, 1937-1939 (2003)
NPL 19: Tokunaga N at al., Circulation, 109, 526-531 (2004)
NPL 20: Ruth R. Wexler at al., Journal of Medicinal Chemistry, 39, 625 (1996)
NPL 21: Am. J. Med., 104(2A), 193 (1998)
NPL 22: F. G. Kathawala et al, 8th Int'l Symp. on Atherosclerosis, Abstract Papers, 445, Rome (1988)
NPL 23: M. Maluccio at al., Transplantation Proceedings, 33, 1820-1821 (2001)
NPL 24: Luo at al., Pathobiology, 78, 285-290 (2011)
NPL 25: Maejima et al., Cancer Research, 62, 4176-4179 (2002)
NPL 26: Wasa et al., Anticancer Research, 31, 123-128 (2011)
NPL 27: Fujita et al., Biochemical and Biophysical Research Communication, 294, 441-447 (2002)
NPL 28: Ino at al., Expert Opinion on Biological Therapy, 6(3), 243-255 (2006)
NPL 29: Tobias Nubel at al., FASEB J., 18(1), 140-2 (2004)

SUMMARY OF INVENTION

Technical Problem

A major objective of the present invention is to provide a novel medicinal composition etc. for suppressing or preventing the metastasis of a malignant tumor, such as carcinoma. Another objective of the present invention is to provide a novel treatment or prevention method for suppressing or preventing the metastasis of a malignant tumor. Another objective of the present invention is to provide a medicinal composition for suppressing or preventing malignant tumor cells from colonizing or invading vascular endothelium, and also a method for suppressing or preventing malignant tumor cells from colonizing or invading vascular endothelium. Other objectives of the present invention will become clear from the following descriptions.

Solution to Problem

The present inventors made extensive examination to solve the problems described above. As a result, they found that treatment with use of an anticancer/antitumor agent can exacerbate or augment the distant metastasis of a cancer and that vasoprotective agents including an angiotensin II receptor antagonist, a HMG-CoA reductase inhibitor, ghrelin, and adrenomedullin can effectively suppress the exacerbation or augmentation of cancer metastasis. Based on the findings, they completed the present invention.

An angiotensin II receptor antagonist, a HMG-CoA reductase inhibitor, ghrelin, and adrenomedullin, as vasoprotective agents, can act protectively on vascular endothelium and thereby effectively inhibit the colonization (adhesion) and invasion of malignant tumor cells to vascular endothelium during the process of metastasis. The adhesion and invasion of malignant tumor cells to vascular endothelium are processes common to metastasis of tumor cells. Therefore, by inhibiting malignant tumor cells from colonizing or invading vascular endothelium, the metastasis of any and all malignant tumors can be suppressed or prevented effectively. Such a metastasis suppressing effect based on a vasoprotective effect is different from the effect that is exerted on a malignant tumor itself and suppresses the growth and metastasis of the tumor by inhibiting angiogenesis or by suppressing DNA synthesis in a malignant tumor.

In the present invention, the metastasis of a malignant tumor (cells) includes distant metastasis of a malignant tumor (cells) and recurrence of a malignant tumor (recurrence at the site of the primary lesion (primary tumor)). The "suppressing or preventing the metastasis of a malignant tumor" means suppressing or preventing distant metastasis of a malignant tumor and/or suppressing or preventing recurrence of a malignant tumor (recurrence at the site of the primary lesion).

That is, the present invention relates to the following.

(1) A medicinal composition for suppressing or preventing the malignant tumor metastasis, the composition comprising, as an active ingredient, at least one kind of vasoprotective agent selected from the following (i) to (iv):
(i) angiotensin II receptor antagonist,
(ii) HMG-CoA reductase inhibitor,
(iii) ghrelin or its derivative, and
(iv) adrenomedullin or its derivative;
or a pharmacologically acceptable salt thereof.

(2) A medicinal composition for suppressing or preventing exacerbation and/or augmentation of metastasis of a malignant tumor caused by an anticancer and/or antitumor agent, the composition comprising, as an active ingredient, at least one kind of vasoprotective agent selected from the following (i) to (iv):
(i) angiotensin II receptor antagonist,
(ii) HMG-CoA reductase inhibitor,
(iii) ghrelin or its derivative, and
(iv) adrenomedullin or its derivative;
or a pharmacologically acceptable salt thereof.

The present invention also relates to a treatment or prevention method for suppressing or preventing the metastasis of a malignant tumor, the method comprising administering, to a patient, an effective amount of at least one kind of vasoprotective agent selected from the above (i) to (iv) and a pharmacologically acceptable salt thereof.

The present invention also relates to a treatment or prevention method for suppressing or preventing exacerbation and/or augmentation of metastasis of a malignant tumor caused by an anticancer and/or antitumor agent, the method comprising administering, to a patient, an effective amount of at least one kind of vasoprotective agent selected from the above (i) to (iv) or a pharmacologically acceptable salt thereof.

The present invention also relates to at least one kind of vasoprotective agent selected from the above (i) to (iv) or a pharmacologically acceptable salt thereof for use in suppressing or preventing the metastasis of a malignant tumor.

The present invention also relates to at least one kind of vasoprotective agent selected from the above (i) to (iv) or a pharmacologically acceptable salt thereof for use in suppressing or preventing exacerbation and/or augmentation of metastasis of a malignant tumor caused by an anticancer and/or antitumor agent.

The present invention also encompasses a medicinal composition for suppressing or preventing the colonization or invasion of malignant tumor cells to vascular endothelium, the composition comprising, as an active ingredient, at least one kind of vasoprotective agent selected from the above (i) to (iv) or a pharmacologically acceptable salt thereof.

The present invention also encompasses a method for suppressing or preventing the colonization or invasion of malignant tumor cells to vascular endothelium, the method comprising administering, to a patient, an effective amount of at least one kind of vasoprotective agent selected from the above (i) to (iv) and a pharmacologically acceptable salt thereof.

The present invention also encompasses at least one kind of vasoprotective agent selected from the above (i) to (iv) or a pharmacologically acceptable salt thereof for use in suppressing or preventing the colonization or invasion of malignant tumor cells to vascular endothelium.

Many of treatment agents against malignant tumor metastasis that are currently used or under development suppress the metastasis through a mechanism of controlling malignant tumor itself. However, the target tissue of the present invention is blood vessels and perivascular tissue (preferably vascular endothelium but not limited to vascular endothelial cells), and the malignant tumor metastasis suppressing effect is exerted by controlling the host side. The treatment method has a completely different mechanism from the conventional one and is a novel technology applicable to any and all malignant tumors regardless of the kind or the nature of the malignant tumor. For example, the present invention can suppress or prevent the colonization or invasion of malignant tumor cells to vascular endothelium, and owing to such a vasoprotective effect, can effectively suppress or prevent the metastasis of a malignant tumor.

Advantageous Effects of Invention

The medicinal composition, the treatment or prevention method, etc. of the present invention have an excellent effect of effectively suppressing or preventing the metastasis of a malignant tumor. In particular, the medicinal composition, the treatment or prevention method, etc. of the present invention can effectively suppress or prevent the metastasis of a malignant tumor through a vasoprotective effect. For example, the medicinal composition and the treatment or prevention method of the present invention can suppress or prevent the colonization or invasion of malignant tumor cells to vascular endothelium in the process of the metastasis of a malignant tumor. Thus, the medicinal composition and the treatment or prevention method of the present invention can exert an excellent metastasis suppressing or preventing effect.

The inventors of the present invention found that administration of an anticancer/antitumor agent (for example, a platinum-based antitumor agent, such as cisplatin (CDDP)) causes vascular endothelial disorder, which promotes the adhesion and invasion of a malignant tumor to vascular endothelium and thus facilitates the metastasis of a malignant tumor. The medicinal composition of the present invention, through its vasoprotective effect, suppresses the adhesion of a malignant tumor to vascular endothelium promoted by administration of an anticancer/antitumor agent, and thus exerts an excellent tumor metastasis suppressing effect (tumor metastasis (distant tumor metastasis) suppressing effect and/or tumor recurrence suppressing effect). Therefore, the use of the medicinal composition of the present invention effectively suppresses or prevents exacerbation and/or augmentation of metastasis of a malignant tumor caused by an anticancer and/or antitumor agent.

Further, the medicinal composition of the present invention, through its vasoprotective effect, can suppress systemic and local adhesion of malignant tumor cells to vascular endothelial cells promoted by surgery, and thus has an excellent tumor metastasis suppressing effect.

With such excellent effects, the present invention can prevent or suppress the metastasis of a malignant tumor, prevent the recurrence after therapeutic resection of a tumor, and also effectively suppress or prevent the metastasis of a malignant tumor that is hard to resect. As a result, an extended survival period can be obtained.

Angiotensin II receptor antagonists, such as telmisartan; HMG-CoA reductase inhibitors, such as pitavastatin; etc. have already been clinically administered to a large number of patients, and the safety has been confirmed. In addition, ghrelin and adrenomedullin are peptides present in the body of mammals including humans. Therefore, the medicinal composition, the treatment or prevention method, etc. of the present invention have little risk of adverse effects and have an excellent tumor metastasis suppressing effect. Thus, the medicinal composition, the treatment or prevention method, etc. of the present invention have both a high safety and an excellent tumor metastasis suppressing effect, and thus are useful in the prevention, treatment, recurrence prevention, etc. of a malignant tumor.

BRIEF DESCRIPTION OF DRAWINGS

FIG. 9A shows photographs (fluorescence micrograph) of fluorescently-labeled A549 cells, and FIG. 9B shows a graph of the number of adherent cancer cells in a field of view (×4.2) obtained with an automated cell counter. In FIG. 9A, spots which appear gray (actually green) are fluorescently-labeled A549-GFP human lung cancer cells. In FIG. 9B, white bars are for the control (without losartan pretreatment), and black bars are for the cases with losartan pretreatment. The vertical axis indicates the number of cancer cells that adhered (*: P<0.05).

DESCRIPTION OF EMBODIMENTS

Figure 1:
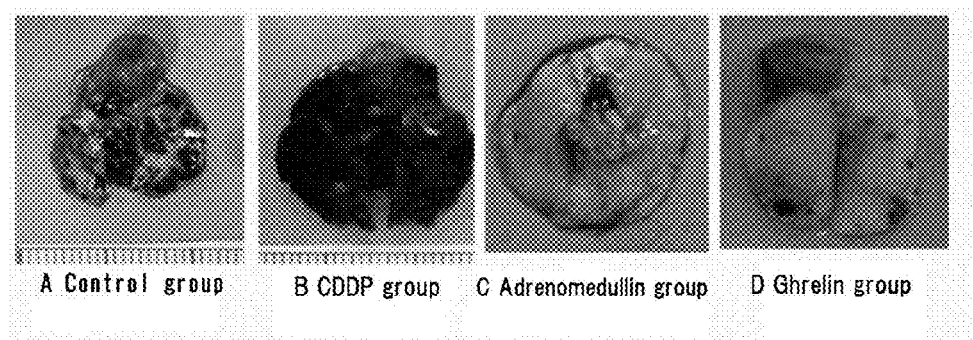
FIG. 1 shows micrographs of lungs at 2 weeks from the injection of mouse melanoma B16-F10 tumor cells into the tail vein of mice in a tail vein injection metastasis test where CDDP, ghrelin, and adrenomedullin were administered (A: the lungs of a mouse as a control, B: the lungs of a mouse to which CDDP was administered, C: the lungs of a mouse to which adrenomedullin was administered, D: the lungs of a mouse to which ghrelin was administered). Black parts are nodules (metastatic foci) formed by metastasized melanoma.

Examples of the vasoprotective agent of the present invention include ghrelin or its derivative, adrenomedullin or its derivative, an angiotensin II receptor antagonist, and a HMG-CoA reductase inhibitor. Among them, preferred are ghrelin or its derivative, adrenomedullin or its derivative, and an angiotensin II receptor antagonist, and particularly preferred is an angiotensin II receptor antagonist.

Ghrelin and its Derivatives:

Ghrelin acts on a growth hormone secretagogue-receptor 1a (GHS-R1a) and thereby promotes secretion of a growth hormone (GH) from the pituitary.

Also, ghrelin has an amino acid sequence usually composed of 28 amino acid residues (or 27 amino acid residues) and having a structure in which the 3rd amino acid residue from the N terminus is acylated with a fatty acid.

In more detail, regarding human or nonhuman mammalian (rat, mouse, porcine, bovine, equine, ovine, canine, etc., for example) ghrelin, the following amino acid sequences and acylated structure are known (aforementioned Patent Literature 1).

```
Human:
                                      (SEQ ID NO: 1)
GSS(n-octanoyl)FLSPEHQRVQQRKESKKPPAKLQPR (SEQ ID NO: 2)
GSS(n-octanoyl)FLSPEHQRVQRKESKKPPAKLQPR Rat:
                                      (SEQ ID NO: 3)
GSS(n-octanoyl)FLSPEHQKAQQRKESKKPPAKLQPR (SEQ ID NO: 4)
GSS(n-octanoyl)FLSPEHQKAQRKESKKPPAKLQPR Mouse:
                                      (SEQ ID NO: 5)
GSS(n-octanoyl)FLSPEHQKAQQRKESKKPPAKLQPR Porcine:
                                      (SEQ ID NO: 6)
GSS(n-octanoyl)FLSPEHQKVQQRKESKKPAAKLKPR Bovine:
                                      (SEQ ID NO: 7)
GSS(n-octanoyl)FLSPEHQKLQRKEAKKPSGRLKPR Ovine:
                                      (SEQ ID NO: 8)
GSS(n-octanoyl)FLSPEHQKLQRKEPKKPSGRLKPR Canine:
                                      (SEQ ID NO: 9)
GSS(n-octanoyl)FLSPEHQKLQQRKESKKPPAKLQPR Equine:
                                      (SEQ ID NO: 10)
GSS(n-butanoyl)FLSPEHHKVQHRKESKKPPAKLKPR
```

(In the above expression, each amino acid residue is represented by the single character expression).

As shown above, ghrelin has a structure in which the side chain hydroxyl group of the amino acid residue (serine (S) residue etc.) at the 3rd position from the N terminus is acylated with a fatty acid, such as octanoic acid and decanoic acid.

For example, human ghrelin is a peptide having an amino acid sequence represented by SEQ ID NO: 1 or 2 in which the amino acid residue (serine residue) at the 3rd position from the amino terminus is a modified amino acid residue having a side chain (hydroxyl group) acylated with a fatty acid (n-octanoic acid).

As the ghrelin, preferred is mammalian ghrelin. For example, human or nonhuman mammalian (rat, mouse, porcine, bovine, equine, ovine, canine, etc.) ghrelin can be used. It is preferred for each individual to use ghrelin of the same species. For example, it is preferred for a human to use human ghrelin.

Examples of the ghrelin derivative include those having a structure similar to that of ghrelin and having effects similar to those of ghrelin, i.e., an agonistic effect on a growth hormone secretagogue-receptor 1a (GHS-R1a) and an effect of promoting secretion of a growth hormone (GH) from the pituitary.

Specific examples of the ghrelin and its derivative include a peptide having a structure selected from the following (1) to (3) and having an agonistic effect on growth hormone secretagogue receptor 1a.

(1) A peptide having an amino acid sequence represented by any one of SEQ ID NOs: 1 to 10 in which the amino acid residue at the 3rd position from the amino terminus is a modified amino acid residue having a side chain acylated with a fatty acid;

(2) A peptide having an amino acid sequence represented by any one of SEQ ID NOs: 1 to 10 in which one to several amino acids are deleted, substituted, and/or added and the amino acid residue at the 3rd position from the amino terminus is a modified amino acid residue having a side chain acylated with a fatty acid;

(3) A peptide having an amino acid sequence represented by any one of SEQ ID NOs: 1 to 10 in which the sequence from the amino terminus to at least the 4th position is conserved, one to several amino acids are deleted, substituted, and/or added not in the conserved sequence, and the amino acid residue at the 3rd position from the amino terminus is a modified amino acid residue having a side chain acylated with a fatty acid.

The "amino acid sequence represented by any one of SEQ ID NOs: 1 to 10" in the above (1) to (3) is, for example in cases where the medicinal composition of the present invention is applied to a human, preferably "an amino acid sequence represented by SEQ ID NO: 1 or 2".

Examples of the fatty acid introduced into the side chain in the above (1) to (3) include fatty acids having 2, 4, 6, 8, 10, 12, 14, 16, or 18 carbon atoms, preferably octanoic acid, decanoic acid, or a monoenoic or polyenoic acid thereof, and more preferably octanoic acid (having 8 carbon atoms, n-octanoic acid, etc.).

In the above (2) and (3), the number of amino acids intended in the "one to several amino acids are deleted, substituted, and/or added" (hereinafter the "deleted, substituted, and/or added" is sometimes referred to as "substituted or the like") is not particularly limited as long as the peptide consisting of the amino acid sequence or its derivative has the desired effect (i.e., an agonistic effect on growth hormone secretagogue receptor 1a). The number is, for example, about 1 to 9, preferably about 1 to 4, more preferably about 1 to 3, still more preferably about 1 to 2, and particularly preferably about 1. As used herein, addition includes insertion. In cases of substitution or the like with amino acids having similar properties (charge and/or polarity), the desired functions are generally retained even if not a few amino acids have been substituted or the like. In cases where substitution or the like occurs at two or more positions, the substitution or the like in all the positions may be deletion only, substitution only, or addition only, or a combination of two or more of deletion, substitution, and addition.

In the amino acid sequence of the ghrelin derivative (for example, the above (2) and (3)), it is preferred that the sequence from the amino terminus to at least the 4th position, preferably to the 5th position, more preferably to the 10th position of the amino acid sequence of natural ghrelin (for example, an amino acid sequence represented by any one of SEQ ID NOs: 1 to 10) is conserved.

Preferably, the amino acid sequence of the ghrelin derivative (for example, the above (2) and (3)) usually has sequence homology of about 70% or more, preferably about 80% or more, more preferably about 90% or more, particularly preferably about 95% or more, and most preferably about 97% or more as compared with the amino acid sequence of natural ghrelin.

Examples of other ghrelin derivatives include those in which the carboxyl terminus of the above-exemplified structure is not ended as a carboxylic acid but amidated so as to mimic a peptide bond. Such a form makes it possible to find out the minimum unit of activity in a shorter amino acid sequence. Another example of other ghrelin derivatives may be the one in which a basic amino acid is added or an amino acid in the form of an amide, such as -Lys-NH$_2$, is introduced to the carboxyl terminus as desired.

Other ghrelin derivatives can be designed appropriately referring to, for example, literature by Matsumoto et al. (Structural similarity of ghrelin derivatives to peptidyl growth hormone secretagogues. Matsumoto, M, Kitajima Y, Iwanami T, Hayashi Y, Tanaka S, Minamitake Y, Hosoda H, Kojima M, Matsuo H, Kangawa K. Biochem Biophys Res Commun. 2001 Jun. 15; 284(3): 655-9).

Whether the ghrelin or its derivative has an agonistic effect on growth hormone secretagogue receptor 1a can be determined by the method described in literature by Matsumoto et al. (Structure-activity relationship of ghrelin: pharmacological study of ghrelin peptides. Matsumoto M, Hosoda H, Kitajima Y, Morozumi N, Minamitake Y, Tanaka, S, Matsuo H, Kojima M, Hayashi Y, and Kangawa K. Biochem Biophys Res Commun. 2001 Sep. 14; 287(1): 142-6.) using, as an indicator, physiological effect via growth hormone secretagogue receptor 1a, such as increase in intracellular calcium ion concentration.

In more detail, for example, ghrelin or its derivative is brought into contact with growth hormone secretagogue receptor 1a, and whether the ghrelin or its derivative increases intracellular calcium ion concentration by binding to the receptor is examined. When the increase in intracellular calcium ion concentration is observed, the compound is regarded as having the agonistic effect.

Examples of other forms of the ghrelin derivative include a nucleic acid which encodes ghrelin or a ghrelin derivative having a peptide structure as described above. The nucleic acid should be designed to express, when administered in vivo, ghrelin or its derivative having the peptide structure as described above.

Ghrelin and its derivative can be synthesized by a conventional method, for example, a chemical synthesis. For example, amino acids with protecting groups are condensed by a liquid phase method and/or a solid phase method for peptide chain elongation, and then the protecting groups are all removed with use of an acid. The resulting crude product is purified by, for example, separation and refinement methods, such as gel filtration, ultrafiltration, dialysis, sodium dodecyl sulfate polyacrylamide gel electrophoresis (SDS-PAGE), and various chromatographic technologies. It is also possible to selectively acylate the side chain of the amino acid in a targeted position with use of an acylating enzyme or an acyltransferase.

Also, a production method as a combination of a conventional recombinant DNA technology and a chemical synthesis may be employed. In this case, for example, a fragment having a modified amino acid residue is produced by chemical synthesis, another fragment not having a modified amino acid residue is separately produced by recombinant DNA technology, and then the fragments are fused together to give ghrelin or its derivative (see aforementioned Patent Literature 1).

Ghrelin and its derivative can be isolated from a natural material.

As used herein, "amino acid" include any and all amino acids, such as L-amino acids, D-amino acids, α-amino acids, β-amino acids, γ-amino acids, natural amino acids, and synthetic amino acids. Preferred are natural amino acids.

Adrenomedullin and its Derivative:

Adrenomedullin is a polypeptide having a vasodilatory effect and an antihypertensive effect (blood pressure lowering effect). In vivo, from a precursor of adrenomedullin, a bioactive form of adrenomedullin (activated adrenomedullin) and PAMP (proadrenomedullin N-terminal 20 peptide) are biosynthesized (hereinafter, PAMP will be included in adrenomedullin derivatives). Adrenomedullin exerts an effect of increasing cAMP in platelets, vascular endothelial cells, and smooth muscle cells, a platelet aggregation suppressing effect, and a strong vasodilatory and antihypertensive effect.

As used herein, adrenomedullin means activated adrenomedullin unless otherwise stated.

Regarding human adrenomedullin and its precursor, the amino acid sequence and the cDNA sequence are known.

SEQ ID NO: 11 shows the cDNA base sequence of an adrenomedullin precursor. SEQ ID NO: 12 shows the amino acid sequence of the adrenomedullin precursor. The amino acid sequence of SEQ ID NO: 12 is an amino acid sequence encoded by the base sequence of SEQ ID NO: 11. SEQ ID NO: 13 shows the amino acid sequence of adrenomedullin (activated form). SEQ ID NO: 14 shows the amino acid sequence of PAMP.

As the adrenomedullin, in addition to human adrenomedullin, adrenomedullin of other animals, such as rat, mouse, porcine, bovine, etc. can be used. Preferred is adrenomedullin of a mammal. It is preferred for each individual to use adrenomedullin of the same species. For example, it is preferred for a human to use human adrenomedullin.

Examples of the adrenomedullin derivative include those having a structure similar to that of adrenomedullin and having effects similar to those of adrenomedullin (an effect of increasing cAMP in platelets or a vasodilatory and/or antihypertensive effect). The adrenomedullin derivative is preferably a polypeptide having an effect of increasing cAMP in platelets, a vasodilatory effect, and an antihypertensive effect.

Adrenomedullin derivatives include precursors of adrenomedullin. Also, adrenomedullin derivatives include PAMP.

Specific examples of the adrenomedullin and its derivative of the present invention include a polypeptide having a structure selected from the following (1) to (3):

(1) a polypeptide having an amino acid sequence represented by SEQ ID NO: 12, 13, or 14, (2) a polypeptide having an amino acid sequence represented by SEQ ID NO: 12, 13, or 14 in which one to several amino acids are deleted, substituted, and/or added, and (3) a polypeptide encoded by a nucleic acid capable of hybridizing to a nucleic acid consisting of a base sequence represented by SEQ ID NO: 11 under stringent condition; and having an effect of increasing cAMP in platelets or a vasodilatory and/or antihypertensive effect.

In the above (3), the nucleic acid may be any of RNA and DNA, but DNA is preferred.

The adrenomedullin or its derivative of the present invention is preferably adrenomedullin (activated form), and more preferably adrenomedullin of a mammal. The above (1) is preferably a polypeptide having an amino acid sequence represented by SEQ ID NO: 13.

In the above (2) of the adrenomedullin or its derivative, the number of amino acids intended in the "one to several amino acids are deleted, substituted, and/or added" is not particularly limited as long as the peptide consisting of the amino acid sequence has the desired function. The number is usually about 30 or less (about 1 to 30), preferably about 15 or less (about 1 to 15), more preferably about 5 or less (about 1 to 5) (for example, preferably about 3 or less (about 1 to 3)), still more preferably about 1 to 2, and particularly preferably about 1. In cases of substitution or the like with amino acids having similar properties (charge and/or polarity), the desired functions are generally retained even if not a few amino acids have been substituted or the like. In cases where substitution or the like occurs at two or more positions, the substitution or the like in all the positions may be deletion only, substitution only, or addition only, or a combination of two or more of deletion, substitution, and addition.

Preferably, the amino acid sequence of the adrenomedullin derivative usually has sequence homology of about 70% or more, preferably about 80% or more, more preferably about 90% or more, particularly preferably about 95% or more, and most preferably about 97% or more as compared with the amino acid sequence of natural adrenomedullin (for example, SEQ ID NO: 12, 13, or 14).

As used herein, stringent condition usually means a condition containing 6 M urea, 0.4% SDS, and 0.5×SSC, or a hybridization condition having similar stringency. Using a condition of higher stringency, for example, a condition containing 6 M urea, 0.4% SDS, and 0.1×SSC, isolation of a DNA with higher homology can be expected. The DNA isolated in the condition has high homology or identity at the amino acid level as compared with the amino acid sequence of the targeted protein.

In the present invention, for example, a nucleic acid capable of hybridizing to a nucleic acid consisting of the base sequence of SEQ ID NO: 11 under stringent condition is preferably a DNA which usually has sequence homology of about 90% or more, preferably about 95% or more, and more preferably about 98% or more with a DNA consisting of a complementary base sequence of SEQ ID NO: 11 and which encodes a polypeptide having an effect of increasing cAMP in platelets or a vasodilatory and/or antihypertensive effect.

The identity of amino acid sequences or base sequences can usually be determined using the algorithm BLAST by Karlin and Altschul. Based on the algorithm of BLAST, programs called BLASTN or BLASTX have been developed. In cases where analysis of a base sequence is performed using BLASTN, the parameters are set as score=100 and wordlength=12, for example. In cases where analysis of an amino acid sequence is performed using BLASTX, the parameters are set as score=50 and wordlength=3, for example. Incases where BLAST and Gapped BLAST programs are used, the default parameters of each program are used. Detailed procedures of these analyzing methods are publicly known.

Whether the adrenomedullin or its derivative has an effect of increasing cAMP in platelets or a vasodilatory and/or antihypertensive effect can be determined by conducting the tests described in literature by Kitamura et al. (Adrenomedullin (11-26): a novel endogenous hypertensive peptide isolated from bovine adrenal medulla. Kitamura K, Matsui E, Kato J, Katoh F, Kita T, Tsuji T, Kangawa K, and Eto T. Peptides. 2001 November; 22(11): 1713-8.) and literature by Champion et al. (Structure-activity relationships of adrenomedullin in the circulation and adrenal gland. Champion H C, Nussdorfer G G, and Kadowitz P J. Regul Pept. 1999 Nov. 30; 85(1): 1-8).

Examples of other forms of the adrenomedullin derivative include a nucleic acid which encodes adrenomedullin or an adrenomedullin derivative having a polypeptide structure as described above. The nucleic acid should be designed to express, when administered in vivo, adrenomedullin or its derivative having the peptide structure as described above.

Adrenomedullin and its derivative can be produced by a conventional recombinant DNA technology or a chemical synthesis, or a combination thereof, etc. Alternatively, it can be isolated from a natural material.

In cases where chemical synthesis is employed, for example, amino acids with protecting groups are condensed by a liquid phase method and/or a solid phase method for peptide chain elongation, and then the protecting groups are all removed with use of an acid. The resulting crude product is purified by, for example, separation and refinement methods, such as gel filtration, ultrafiltration, dialysis, sodium dodecyl sulfate polyacrylamide gel electrophoresis (SDS-PAGE), and various chromatographic technologies, to give adrenomedullin or its derivative.

Angiotensin II Receptor Antagonist:

An angiotensin II receptor antagonist has an effect of hindering angiotensin II from binding to an angiotensin II receptor (AT1 receptor). The angiotensin II receptor antagonist used as an active ingredient of the present invention may be any agent as long as it has the effect.

Examples of the angiotensin II receptor antagonist in the present invention include losartan, eprosartan, candesartan, candesartan cilexetil, valsartan, telmisartan, irbesartan, tasosartan, olmesartan, olmesartan medoxomil, and azilsartan. Preferred examples of the angiotensin II receptor antagonist in the present invention include one or more kinds of eprosartan, valsartan, telmisartan, irbesartan, tasosartan, olmesartan, olmesartan medoxomil, and azilsartan, and more preferred examples include one or more kinds of valsartan, telmisartan, irbesartan, azilsartan, and olmesartan medoxomil. In cases where the angiotensin II receptor antagonist is administered (in combination) with an anticancer and/or antitumor agent, as described later, preferred are one or more kinds of losartan, candesartan cilexetil, valsartan, telmisartan, irbesartan, azilsartan, and olmesartan medoxomil. As the angiotensin II receptor antagonist in the present invention, particularly preferred is telmisartan.

HMG-CoA Reductase Inhibitor:

A HMG-CoA reductase inhibitor has an effect of specifically inhibiting HMG-CoA reductase. The HMG-CoA reductase inhibitor used as an active ingredient of the present invention may be any agent as long as it has the effect.

Examples of the HMG-CoA reductase inhibitor in the present invention include natural substances derived from microorganisms, semisynthetic substances derived from such natural substances, and completely synthetic compounds, and specific examples thereof include pravastatin, lovastatin, simvastatin, fluvastatin, rivastatin, atorvastatin, pitavastatin, and rosuvastatin. Among them, preferred are pravastatin, simvastatin, fluvastatin, rivastatin, atorvastatin, pitavastatin, and rosuvastatin, and particularly preferred is pitavastatin.

As the above angiotensin II receptor antagonist and the above HMG-CoA reductase inhibitor, commercially available agents or compounds may be used, for example.

The active ingredient in the present invention may be in a free form or in the form of a pharmacologically acceptable salt thereof. Examples of the salt include a salt with an inorganic base, a salt with an organic base, a salt with an inorganic acid, a salt with an organic acid, a salt with a basic or acidic amino acid, etc.

Preferred examples of the salt with an inorganic base include alkali metal salts, such as a sodium salt and a potassium salt; alkaline earth metal salts, such as a calcium salt and a magnesium salt; an aluminum salt; an ammonium salt; and the like.

Preferred examples of the salt with an organic base include salts with trimethylamine, triethylamine, pyridine, picoline, ethanolamine, diethanolamine, triethanolamine, dicyclohexylamine, N,N'-dibenzylethylenediamine, and the like.

Preferred examples of the salt with an inorganic acid include salts with hydrochloric acid, hydrobromic acid, nitric acid, sulfuric acid, phosphoric acid, and the like.

Preferred examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferred examples of the salt with a basic amino acid include salts with arginine, lysine, ornithine, and the like; and preferred examples of the salt with an acidic amino acid include salts with aspartic acid, glutamic acid, and the like.

The medicinal composition of the present invention is not particularly limited as long as it comprises the above-mentioned vasoprotective agent or a pharmacologically acceptable salt thereof as an active ingredient. The composition may comprise a publicly known pharmacologically acceptable inert carrier, excipient, diluent, etc. In the treatment or prevention method for suppressing or preventing the metastasis of a malignant tumor, it is preferred that a medicinal composition comprising the vasoprotective agent is administered to a patient.

Utilizing the medicinal composition, the method for suppressing or preventing the metastasis of a malignant tumor, and the treatment or prevention method of the present invention, the metastasis of a malignant tumor can be suitably suppressed or prevented. Further, the present invention exerts an excellent metastasis suppressing effect even on a malignant tumor of which the metastasis has been exacerbated or augmented by an anticancer and/or antitumor agent (for example, a platinum-based antitumor agent, such as cisplatin). Similarly, the present invention exerts an excellent effect even on the metastasis of a malignant tumor of a patient who has undergone resection of a tumor, radiotherapy, or laser ablation treatment. Therefore, according to the present invention, it is also possible to suppress or prevent the metastasis of a malignant tumor.

Usually, the metastasis suppressing effect according to the present invention is exerted in a manner other than cell-killing or cytostatic action on a malignant tumor itself. The effect is different from that of common anticancer/antitumor agents which acts on the malignant tumor side, and is an effect of protecting blood vessels or other vessels, that is, an effect exerted on the host (for example, a malignant tumor patient) side.

Since the effect of the present invention is exerted on the host side, the present invention can exert an excellent metastasis suppressing effect on any and all kinds of malignant tumors regardless of the kind of the malignant tumor (for example, carcinoma).

The medicinal composition for suppressing or preventing the metastasis of a malignant tumor is suitable also as a medicinal composition for suppressing or preventing malignant tumor cells from colonizing or invading vascular endothelium.

The method for suppressing or preventing the metastasis of a malignant tumor, and the treatment or prevention method of the present invention are suitable also as a method for suppressing or preventing malignant tumor cells from colonizing or invading vascular endothelium.

The medicinal composition, the method for suppressing or preventing the metastasis of a malignant tumor, and the treatment or prevention method of the present invention can be suitably used for suppressing or preventing the metastasis of any and all kinds of malignant tumors. In particular, they are suitable for suppressing or preventing colonization (adhesion) or invasion of malignant tumor cells to vascular endothelium during the process of blood-borne metastasis.

Because of these excellent effects, the present invention is useful not only for suppression and prevention of the metastasis of a malignant tumor and for prevention etc. of the recurrence after therapeutic resection of a tumor but also for effective suppression or prevention of the metastasis of a malignant tumor that is hard to resect.

In addition, angiotensin II receptor antagonists, such as telmisartan; HMG-CoA reductase inhibitors, such as pitavastatin; etc. have already been clinically administered to a large number of patients, and the safety has been confirmed. Therefore, the medicinal composition and the treatment or prevention method of the present invention advantageously have little risk of adverse effects.

An objective of the present invention is to suppress or prevent the metastasis of a malignant tumor, and the intended patients are usually those with a malignant tumor. The kind of the malignant tumor is not particularly limited, and examples thereof include various types, for example, epithelial malignant tumor, such as carcinoma; non-epithelial malignant tumor, such as sarcoma; and melanoma.

Examples of the malignant tumor include lung cancer (non-small cell lung cancer, small cell lung cancer, malignant mesothelioma, etc.), gastric cancer, colon cancer, liver cancer, kidney cancer, bladder cancer, pancreatic cancer, thyroid cancer, breast cancer, uterine cancer, ovarian cancer, prostatic cancer, bone tumor, brain tumor, etc.

An objective of the present invention is to suppress or prevent the metastasis of a malignant tumor, and the site of metastasis can be any and all organs and tissues throughout the body because malignant tumor cells released from a primary tumor (primary lesion) enter the blood circulatory system or the lymph system and are diffused to other parts of the body. Malignant tumor cells tend to metastasize to, in particular, organs and tissues where thin blood vessels such as capillary are dense and the blood flow is high. In the case of a solid tumor, examples of the most common metastasis site include the lung, the bone, the liver, and the brain. In particular, the lung and the liver are important as sites of metastasis. According to the present invention, the metastasis to, for example, tissues or organs, such as the lung, the bone, the liver, and the brain, more preferably to the lung or the liver can be suppressed or prevented effectively.

The malignant tumor may be a primary tumor or a metastatic tumor, and the timing of the administration of the medicinal composition of the present invention may be anytime after the detection of a malignant tumor, such as carcinoma. In view of the general practice for metastasis suppression, continuous administration or regular administration at certain intervals is preferred.

The medicinal composition of the present invention is preferably administered to a patient who is to undergo or who has undergone resection of a malignant tumor. A patient who is receiving or who has received administration of an anticancer/antitumor agent is also preferable as a subject of administration of the medicinal composition of the present invention. The anticancer/antitumor agent is, for example, one or more kinds of anticancer/antitumor agents that are other than the medicinal composition of the present invention and can be used together with the medicinal composition of the present invention, and such other anticancer/antitumor agents will be described later.

In cases where resection of a malignant tumor, such as carcinoma, is conducted, efficient suppression of the metastasis of the malignant tumor can be achieved as follows. The medicinal composition of the present invention is administered to the patient for protection of blood vessels before the resection, and then the resection is performed. The blood vessel protection should be continued until the influence of inflammatory cytokines produced after the resection disappears. Usually, the administration is started about 1 week or more, preferably about 10 days or more before the resection, and continued until about 1 week or more, preferably about 10 days or more after the resection.

The dosage form and the administration route of the medicinal composition of the present invention are not particularly limited, and one or more kinds of oral or parenteral agents can be selected depending on the conditions of the patient. One or more of oral agents and one or more of parenteral agents can be used in combination.

The medicinal composition of the present invention can be used in combination with at least one of other metastasis-suppressing agents. As such a metastasis-suppressing agent, for example, a GC-A agonist, a GC-B agonist, a NEP inhibitor, a PDE5 inhibitor, a NO donor, an eNOS activator, a GC-C agonist, a cGMP analog, etc. described in WO 2012/118042 can preferably be used.

In cases where one or more of other metastasis-suppressing agents are parenterally, for example intravenously administered, continuous administration with the use of an infusion pump, a catheter, etc. is preferably performed. The duration of the continuous administration is several hours to several days (for example, about 3 to 14 days, preferably about 3 to 7 days).

In cases where the medicinal composition of the present invention and other metastasis-suppressing agent are used in combination, each can be administered over the above-mentioned administration duration appropriate for the administration method.

In the present invention, usually, the active ingredient may be mixed with a publicly known pharmacologically acceptable inert carrier, excipient, diluent, etc. to be formed into a medicinal composition, and administered to an individual by an administration method conventionally used in the pharmaceutical field, i.e., oral administration or parenteral administration, such as permucosal administration, intravenous administration, intramuscular administration, and subcutaneous administration.

For example, in cases where the active ingredient is a peptide substance, it may be orally administered as a formulation resistant to degradation in the digestive tract, for example, a microcapsule formulation based on liposomes encapsulating the peptide as the active ingredient. The administration can be performed not through the mucosa of the digestive tract but through, for example, the rectal, intranasal, or sublingual mucosa. In this case, the active ingredient can be administered to an individual in the form of, for example, a suppository, a nasal spray, an inhalant, a sublingual tablet, etc. In the present invention, such formulations may be used that the peptide retention in the blood is improved by adopting various controlled-release formulations or long-acting formulations which comprise a biodegradable polymer represented by polysaccharide such as dextran, polyamine, PEG, etc. as a carrier.

When the active ingredient is in the form of a nucleic acid encoding a peptide substance, the nucleic acid (such as a gene encoding a peptide substance) may be introduced into a patient via intravenous injection, intramuscular injection, local injection, or the like using a viral vector such as a retrovirus, an adenovirus, and an adeno-associated virus, or using a plasmid vector etc.

The dosage amount of the substance used as an active ingredient of the medicinal composition of the present invention varies with the type of disease (malignant tumor); the age, body weight, and degree of the symptoms of the individual (patient); and the route of administration, and can be selected as appropriate, but generally the upper limit of the daily dosage of each active ingredient is, for example, usually about 100 mg/kg or less, preferably about 50 mg/kg or less, and more preferably about 1 mg/kg or less. The lower limit of the daily dosage of each active ingredient is, for example, usually about 0.1 µg/kg or more, preferably about 0.5 µg/kg or more, and more preferably about 1 µg/kg or more. The dosage amount is expressed as an amount per kilogram of body weight.

In cases where the active ingredient is ghrelin or its derivative, the administration rate is, for example, continuous administration of about 0.1 µg/kg/min or less, preferably about 0.08 µg/kg/min or less, or the like.

In cases where the active ingredient is adrenomedullin or its derivative, the administration rate is usually continuous administration of about 0.1 µg/kg/min or less, preferably about 0.05 µg/kg/min or less, or the like.

The duration of the continuous administration of ghrelin, adrenomedullin, or a derivative thereof is usually about one day or longer, and preferably about 1 day to about 2 weeks. In the continuous administration, a preferred administration method is intravenous administration, or the like.

The administration frequency of the active ingredient in the medicinal composition, the treatment or prevention method, or the like of the present invention is not particularly limited and varies with the active ingredient to be used, the route of administration, and the specific disease to be treated.

In cases where ghrelin, adrenomedullin, or a derivative thereof is orally administered, a preferable frequency of the administration is for example about 4 times or less daily. In cases of parenteral administration, for example intravenous administration, continuous administration with the use of an infusion pump, a catheter, etc. is preferred.

In cases where an angiotensin II receptor antagonist or a HMG-CoA reductase inhibitor is orally administered, the agent is preferably administered, for example, about once to 3 times daily. For example, in cases where an angiotensin II receptor antagonist or a HMG-CoA reductase inhibitor is used, the agent is preferably orally administered in a daily amount of about 1 to 100 mg/kg body weight of the active ingredient, and the dosage amount is comparable to or less than that used for hypertension or hypercholesterolemia.

The medicinal composition, the treatment or prevention method, or the like of the present invention, when combined with at least one of other usually used anticancer and/or antitumor agents, can achieve more effective treatment of a malignant tumor. The present invention encompasses such a combination treatment with another anticancer and/or antitumor agent. An example of such a combination treatment is an embodiment in which the medicinal composition of the present invention is administered to a patient who is receiving or who has received administration of an anticancer/antitumor agent. Since the medicinal composition of the present invention can control the metastasis and invasion of tumor cells, appropriate administration of the medicinal composition during a treatment using another anticancer and/or antitumor agent can increase the efficiency of the treatment with the anticancer and/or antitumor agent and can improve the prognosis of the treatment.

By using the vasoprotective agent or a pharmacologically acceptable salt thereof with at least one of other usually used anticancer and/or antitumor agents, an effect of effectively suppressing or preventing exacerbation and/or augmentation of metastasis of a malignant tumor caused by the anticancer and/or antitumor agent can also be obtained.

The medicinal composition of the present invention is preferably used for suppressing or preventing exacerbation and/or augmentation of metastasis of a malignant tumor caused by an anticancer and/or antitumor agent.

The present invention encompasses a method for suppressing or preventing exacerbation and/or augmentation of metastasis of a malignant tumor caused by an anticancer and/or antitumor agent, the method comprising administering an effective amount of a vasoprotective agent or a pharmacologically acceptable salt thereof to a patient.

In cases where the medicinal composition of the present invention is administered (in combination) with an anticancer and/or antitumor agent, the dosage amount of the anticancer and/or antitumor agent is not particularly limited and can be set as appropriate depending on the type of the agent, the type of disease (malignant tumor); the age, body weight, and degree of the symptoms of the individual (patient); and the route of administration, and is a usually used amount.

In cases where the medicinal composition of the present invention is administered (in combination) with an anticancer and/or antitumor agent, the dosage amount of the medicinal composition of the present invention varies with the type of disease (malignant tumor); the age, body weight, and degree of the symptoms of the individual (patient); and the route of administration, and is appropriately selected. Regarding the dosage amount of the vasoprotective agent or a pharmacologically acceptable salt thereof as an active ingredient, in cases where an angiotensin II receptor antagonist or a HMG-CoA reductase inhibitor is used for example, preferably about 1 to 100 mg/kg body weight of the active ingredient is orally administered daily, and the dosage amount is comparable to or less than that used for hypertension or hypercholesterolemia.

Incases where an anticancer/antitumor agent (for example, a platinum-based antitumor agent, such as cisplatin) is administered, efficient suppression of the metastasis (distant metastasis and recurrence) of a malignant tumor can be achieved as follows. The medicinal composition of the present invention is administered to the patient for preliminary protection of blood vessels, and then the anticancer/antitumor agent is administered. The blood vessel protection should be continued until the anticancer/antitumor agent is eliminated from the body. Usually, the administration of the medicinal composition of the present invention is started about 1 week or more, preferably about 10 days or more before the start of the administration of the anticancer/antitumor agent, and continued until about 1 week or more, preferably about 10 days or more after the end of the administration of the anticancer/antitumor agent.

Incases where an anticancer/antitumor agent (for example, a platinum-based antitumor agent, such as cisplatin) is administered, one or more kinds of oral or parenteral agents can be selected as the medicinal composition for the present invention depending on the conditions of the patient. One or more of oral agents and one or more of parenteral agents can be used in combination.

The medicinal composition of the present invention can be used in combination with at least one of said other metastasis-suppressing agents.

In cases where an anticancer/antitumor agent (for example, a platinum-based antitumor agent, such as cisplatin) is administered, the medicinal composition of the present invention and other metastasis-suppressing agents used in combination can be administered at the same time or at different times.

In such a combined administration, the administration of the medicinal composition of the present invention is usually started about 1 week or more, preferably about 10 days or more before the start of the administration of the anticancer/antitumor agent, and continued until about 1 week or more, preferably about 10 days or more after the end of the administration of the anticancer/antitumor agent.

The dosage form and the administration route of the medicinal composition of the present invention are not particularly limited, and one or more kinds of oral or parenteral agents can be selected depending on the conditions of the patient. One or more of oral agents and one or more of parenteral agents can be used in combination.

In such a combined administration, in cases where one or more of other metastasis-suppressing agents are parenterally, for example intravenously administered, continuous administration with the use of an infusion pump, a catheter, etc. is preferably performed. The duration of the continuous administration is about several hours to several days (for example, about 3 to 14 days, preferably about 3 to 7 days).

In cases where the medicinal composition of the present invention and another metastasis-suppressing agent are used in combination, each can be administered over the above-mentioned administration duration appropriate for the administration method.

In cases where the medicinal composition of the present invention or another metastasis-suppressing agent is administered, the administration is preferably performed depending on the condition of the patient as follows. For example, before resection or administration of an anticancer/antitumor agent, the medicinal composition of the present invention (for example, an angiotensin II receptor antagonist or a HMG-CoA reductase inhibitor) or said another metastasis-suppressing agent is orally administered. After the resection or the administration of the anticancer/antitumor agent, i.e., during a period in which oral administration of medicinal agents etc. cannot be performed, a medicinal composition of the present invention (for example, ghrelin or its derivative, or adrenomedullin or its derivative) or said another metastasis-suppressing agent is parenterally administered, and after recovery, the medicinal composition of the present invention or another metastasis-suppressing agent is orally administered.

Examples of the anticancer/antitumor agent used in combination with the medicinal composition of the present invention include an alkylating agent, an antimetabolite, an antitumor antibiotic, an antitumor plant constituent, a BRM (biological response control substance), a hormone, a vitamin, an anticancer antibody, a molecular target agent, a platinum-based antitumor agent, other anticancer/antitumor agents, etc. Among them, preferred as an anticancer/antitumor agent used in combination with the medicinal composition of the present invention is a platinum-based antitumor agent.

More specifically, examples of the alkylating agent include alkylating agents, such as nitrogen mustard, nitrogen mustard N-oxide and chlorambucil; aziridine alkylating agents, such as carboquone and thiotepa; epoxide alkylating agents, such as dibromomannitol and dibromodulcitol; nitrosourea alkylating agents, such as carmustine, lomustine, semustine, nimustine hydrochloride, streptozocin, chlorozotocin, and ranimustine; busulfan; improsulfan tosilate; dacarbazine; etc.

Examples of various antimetabolites include purine antimetabolites, such as 6-mercaptopurine, 6-thioguanine, and thioinosine; pyrimidine antimetabolites, such as fluorouracil, tegafur, tegafur-uracil, carmofur, doxifluridine, broxuridine, cytarabine, and enocitabine; folate antimetabolites, such as methotrexate and trimetrexate; etc.

Examples of the antitumor antibiotic include anthracycline antibiotic antitumor agents, such as mitomycin-C, bleomycin, peplomycin, daunorubicin, aclarubicin, doxorubicin, pirarubicin, THP-adriamycin, 4'-epidoxorubicin, and epirubicin; chromomycin A3; actinomycin-D; etc.

Examples of the antitumor plant constituent include vinca alkaloids, such as vindesine, vincristine, and vinblastine; taxanes, such as paclitaxel and docetaxel; epipodophyllotoxins, such as etoposide and teniposide.

Examples of the BRM include a tumor necrosis factor, indomethacin, etc.

Examples of the hormone include hydrocortisone, dexamethasone, methylprednisolone, prednisolone, prasterone, betamethasone, triamcinolone, oxymetholone, nandrolone, methenolone, fosfestrol, ethinylestradiol, chlormadinone, medroxyprogesterone, etc.

Examples of the vitamin include vitamin C, vitamin A, etc.

Examples of the antitumor antibody and the molecular target agent include trastuzumab, rituximab, cetuximab, nimotuzumab, denosumab, bevacizumab, infliximab, imatinib mesylate, gefitinib, erlotinib, sunitinib, lapatinib, sorafenib, etc.

Examples of the platinum-based antitumor agent include cisplatin, carboplatin, oxaliplatin, etc. Among them, cisplatin is preferred.

Examples of other anticancer/antitumor agents include tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, krestin, etc.

In the present invention, when additional anticancer/antitumor agents (or metastasis-suppressing agents) are administered in combination with the vasoprotective agent, one or more kinds of the vasoprotective agents and the additional anticancer/antitumor agents (or metastasis-suppressing agents) may be contained as active ingredients in a single formulation or in separate formulations.

In cases where the medicinal composition of the present invention is used with an anticancer and/or antitumor agent, the combination of the vasoprotective agent or a pharmacologically acceptable salt thereof and the anticancer and/or antitumor agent is not particularly limited, but for example, when the anticancer or antitumor agent is a platinum-based antitumor agent, such as cisplatin, the vasoprotective agent is preferably an angiotensin II receptor antagonist or a HMG-CoA reductase inhibitor. Angiotensin II receptor antagonists and HMG-CoA reductase inhibitors can effectively suppress exacerbation and/or augmentation of metastasis of a malignant tumor caused by a platinum-based antitumor agent. The angiotensin II receptor antagonist is preferably one or more kinds of telmisartan, valsartan, losartan, olmesartan medoxomil, azilsartan, candesartan cilexetil, and irbesartan. The HMG-CoA reductase inhibitor is preferably pitavastatin. The platinum-based antitumor agent to be used in combination with the angiotensin II receptor antagonist or the HMG-CoA reductase inhibitor is preferably cisplatin.

In the present invention, "combined administration" of multiple active ingredients or drugs means that a subject to receive the administration takes all the combined active ingredients or drugs into the body in a certain period of time. The active ingredients may be administered as a single formulation containing all the ingredients (so-called compounding agent). Alternatively, the active ingredients may be separately formulated into separate formulations and then separately administered (so-called administration based on combined use). In cases where the active ingredients are separately formulated, the timing of the administration is not particularly limited. The formulations may be administered simultaneously, on the same day at certain time intervals, or on different days. In cases where two or more active ingredients are administered at different timings of the same day or on different days, the order of administration of the active ingredients is not particularly limited. Normally, each formulation is administered according to each administration method, and therefore the frequency of the administration method may be the same or different among the formulations. In cases where each active ingredient is separately formulated, the administration method (route of administration) may be the same or different among the formulations. It is not necessary that all the active ingredients are present in the body at the same time. As long as all the active ingredients are taken into the body during a certain period of time (for example, one month, preferably one week, more preferably several days, still more preferably one day), it is allowable that one active ingredient has already disappeared from the body when another active ingredient is administered.

EXAMPLES

Hereinafter, the invention will be specifically described by referring to the Examples below. The Examples are merely illustrative examples of the embodiments of the present invention, and the present invention is not limited thereto.

The experimental materials used in the Examples below were obtained and prepared as follows.

The cisplatin (CDDP) used was CISPLATIN inj. "Maruko" (Nichi-Iko Pharmaceutical). The osmotic pumps used were MODEL2002 (for 14-day administration) made by ALZET (Cupertino, Calif.). Ghrelin (a peptide consisting of the amino acid sequence of SEQ ID NO: 1 in which the side chain hydroxyl group of the serine residue at the 3rd position from the amino terminus is octanoylated) andadrenomedullin (SEQIDNO: 13) were obtained, each in the form of a lyophilized product, from Asubio Pharma Co., Ltd., and the lyophilized products were separately dissolved in physiological saline. After the concentrations were adjusted as appropriate, the solutions were used in the following experiments. The chi-squared test was used to determine whether there was a significant difference (*: P<0.05) in the Examples.

Example 1

Lung Metastasis Suppressing Effects of Various Bioactive Peptides and Agents in Blood-Borne Metastasis Model Established by Injection of Mouse Melanoma to Mouse Tail Vein Six-week-old male C56BL/6N mice (purchased from Japan SLC, Inc.) were used. Mouse melanoma B16-F10 was purchased from ATCC, and cultured in DMEM (Life Technologies Corp.) containing 10% FCS under 5% $CO_2$ at 37° C. The cells in a subconfluent state were treated with EDTA-trypsin, centrifuged, and then suspended in serum free DMEM so as to be $5\times10^6$ cells/mL. The melanoma cell suspension (100 μL/mouse, $5\times10^5$ cells) was injected to the tail vein of the mice.

Figure 2:
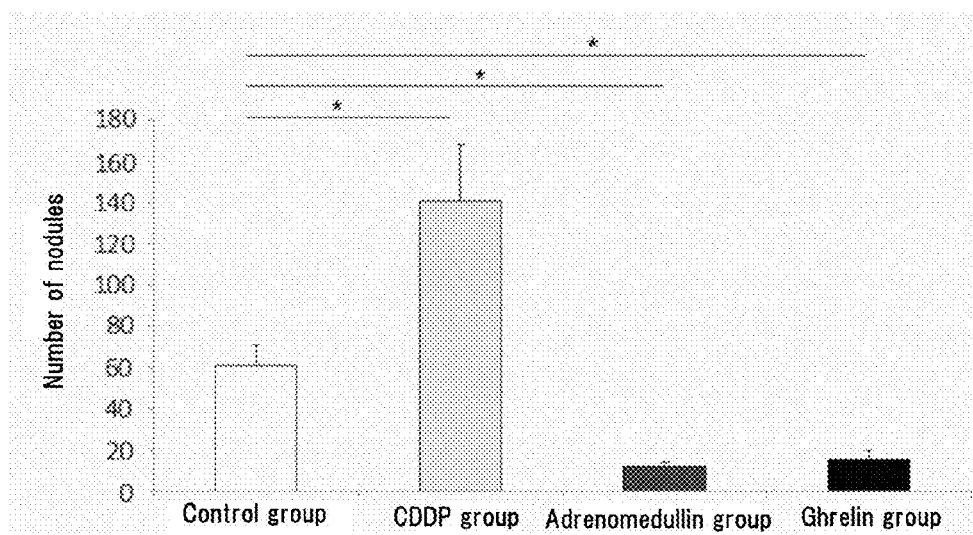
FIG. 2 shows a graph showing the number of nodules formed due to lung metastasis at 2 weeks from the injection of mouse melanoma B16-F10 tumor cells into the tail vein of mice in a tail vein injection metastasis test where CDDP, ghrelin, and adrenomedullin were administered. The vertical axis indicates the number of nodules formed in the lungs per individual. Each bar is for, from the left to the right, the control group (physiological saline), the CDDP group (5 mg/kg), the adrenomedullin group (0.05 µg/kg/min), and the ghrelin group (0.08 µg/kg/min).

For the CDDP group, 5 mg/kg of CDDP was injected, as pretreatment, to the tail vein of the mice 2 days before the injection of the melanoma cells into the tail vein. For the control group, an osmotic pump containing 0.9% physiological saline was subcutaneously implanted in the back of each mouse on the day before the injection of the melanoma cells into the tail vein. Similarly, for the adrenomedullin group, an osmotic pump containing adrenomedullin prepared for administration at 0.05 μg/kg/min was subcutaneously implanted into each mouse, and for the ghrelin group, an osmotic pump containing ghrelin prepared for administration at 0.08 μg/kg/min was subcutaneously implanted into each mouse. The tail vein injection of the melanoma cells was performed as above and the drug administration was continued for 2 weeks. The condition of the lung metastasis of the tumor cells 2 weeks after the tumor cell injection was observed (FIG. 1). FIG. 2 shows the number of observed nodules per animal formed due to lung metastasis.

To the angiotensin II receptor antagonist group, a 0.5% methylcellulose aqueous solution prepared so as to contain 2 mg/kg or 8 mg/kg of telmisartan was orally given for 4 days before the start of the experiment (before the injection of tumor cells to mice), and to the pitavastatin group, a 0.5% methylcellulose aqueous solution prepared so as to contain 20 mg/kg of pitavastatin was orally given for the same period. After the injection of tumor cells, the oral intake of methylcellulose aqueous solutions containing telmisartan or pitavastatin in the above doses in the angiotensin II receptor antagonist group and the pitavastatin group was continued until the end of the experiment. To the control group, a 0.5% methylcellulose aqueous solution not containing any of the agents was orally given before the start of the experiment. Also, as reference example, angiotensin II was administered at 1 μg/kg/min, and then the experiment was conducted in the same way. The sample size of each group was n=5.

Figure 3:
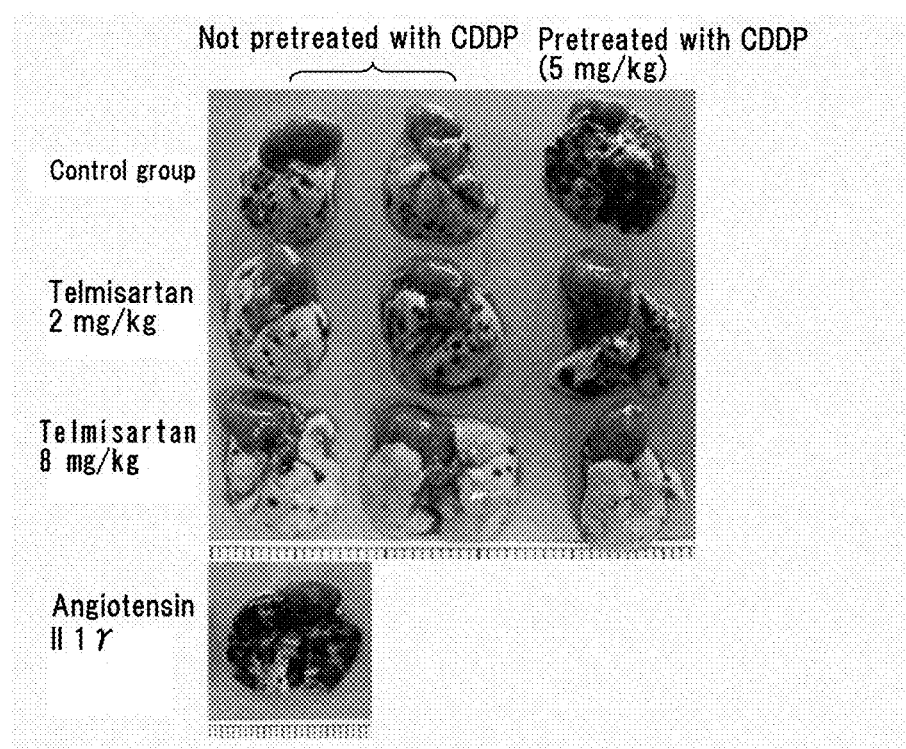
FIG. 3 shows micrographs of lungs at 14 days from the injection of mouse melanoma B16-F10 tumor cells into the tail vein of mice in a tail vein injection metastasis test where telmisartan (2 mg/kg or 8 mg/kg) and angiotensin II (1 µg/kg/min) were administered alone, or telmisartan (2 mg/kg or 8 mg/kg) was administered before pretreatment with CDDP (5 mg/kg). Black parts are nodules (metastatic foci) formed by metastasized melanoma.
Figure 4:
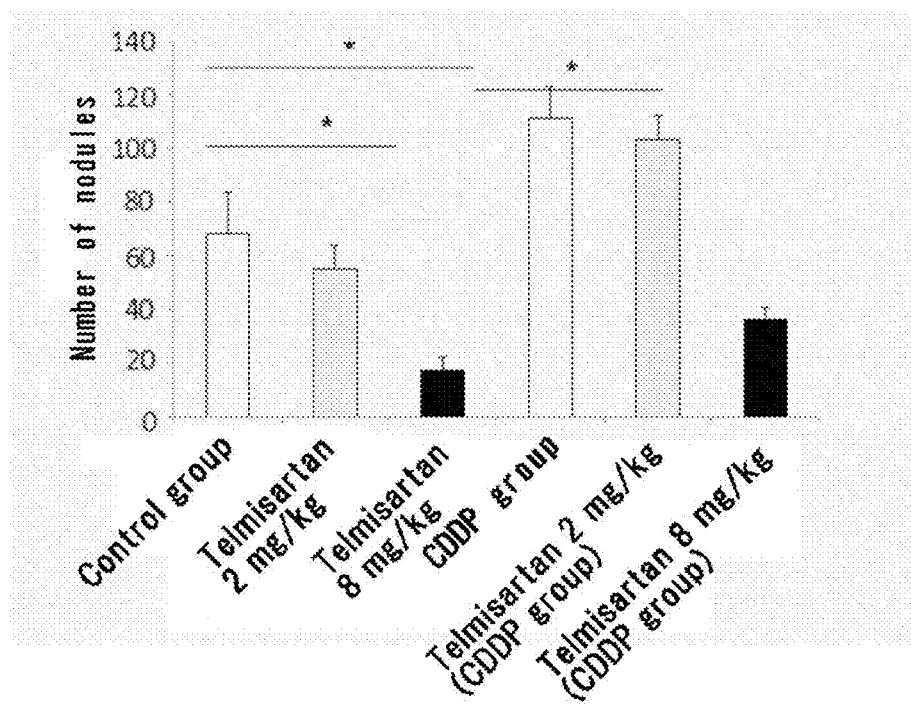
FIG. 4 shows a graph showing the number of nodules formed due to lung metastasis at 14 days from the injection of mouse melanoma B16-F10 tumor cells into the tail vein of mice in a tail vein injection metastasis test where telmisartan (2 mg/kg or 8 mg/kg) was administered alone, or telmisartan (2 mg/kg or 8 mg/kg) was administered before pretreatment with CDDP (5 mg/kg). The vertical axis indicates the number of nodules formed in the lungs per individual. Each bar is for, from the left to the right, the control group (physiological saline), the telmisartan 2 mg/kg group, the telmisartan 8 mg/kg group, the CDDP group (5 mg/kg), the group to which telmisartan 2 mg/kg was administered before CDDP pretreatment, and the group to which telmisartan 8 mg/kg was administered before CDDP pretreatment.

As a result, as shown in FIGS. 3 and 4, the lung metastasis of melanoma was significantly suppressed in the telmisartan 8 mg/kg group. Also, as shown in FIG. 4, the lung metastasis of melanoma was significantly increased in the CDDP group as compared to the control group. In contrast, in both of the telmisartan 2 mg/kg group and the telmisartan 8 mg/kg group, the exacerbation by CDDP was suppressed. The telmisartan 2 mg/kg (CDDP group) and the telmisartan 8 mg/kg (CDDP group) shown in FIGS. 3 and 4 are groups to which 2 mg/kg or 8 mg/kg of telmisartan was given in the manner described above before CDDP was injected as pretreatment. The pitavastatin (CDDP group) is the group to which pitavastatin was given in the manner described above before CDDP was injected as pretreatment.

Figure 5:
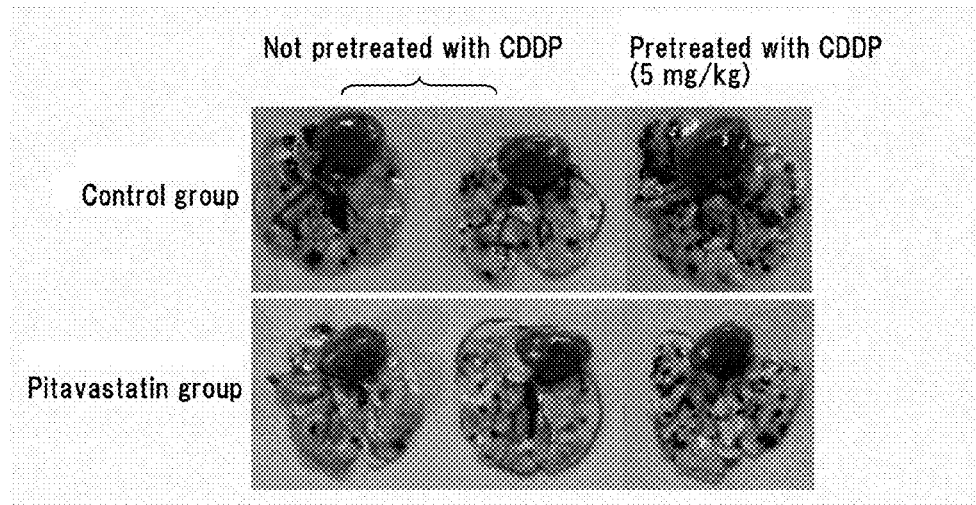
FIG. 5 shows micrographs of lungs at 14 days from the injection of mouse melanoma B16-F10 tumor cells into the tail vein of mice in a tail vein injection metastasis test where pitavastatin (20 mg/kg) was administered alone, or pitavastatin (20 mg/kg) was administered before pretreatment with CDDP (5 mg/kg). Black parts are nodules (metastatic foci) formed by metastasized melanoma.
Figure 6:
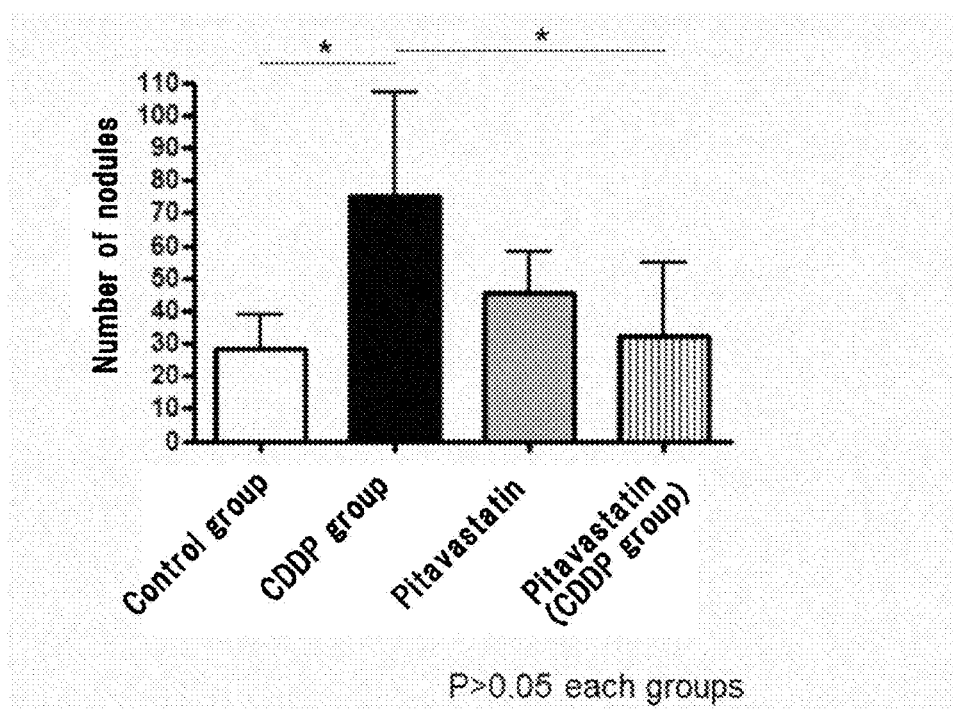
FIG. 6 shows a graph showing the number of nodules formed due to lung metastasis at 14 days from the injection of mouse melanoma B16-F10 tumor cells into the tail vein of mice in a tail vein injection metastasis test where pitavastatin (20 mg/kg) was administered alone, or pitavastatin (20 mg/kg) was administered before pretreatment with CDDP (5 mg/kg). The vertical axis indicates the number of nodules formed in the lungs per individual. Each bar is for, from the left to the right, the control group (physiological saline), the CDDP group (5 mg/kg), the pitavastatin group (20 mg/kg), and the group to which pitavastatin (20 mg/kg) was administered before CDDP pretreatment.

Meanwhile, as shown in FIGS. 5 and 6, the exacerbation of the lung metastasis by CDDP was significantly suppressed in the pitavastatin group.

Example 2

Lung Metastasis Suppressing Effects of Various Agents in Blood-Borne Metastasis Model Established by Injection of Mouse Melanoma to Mouse Tail Vein Eight-week-old male C57BL6 mice (purchased from Japan SLC, Inc.) were used. Mouse melanoma B16-F10 was purchased from ATCC, and cultured in DMEM (Life Technologies Corp.) containing 10% FCS under 5% $CO_2$ at 37° C. The cells in a subconfluent state were treated with EDTA-trypsin, centrifuged, and then suspended in serum free DMEM so as to be $5\times10^6$ cells/mL. The melanoma cell suspension (100 μL/mouse, $3\times10^5$ cells) was injected to the tail vein of the mice.

As pretreatment, 5 mg/kg of cisplatin (CDDP) was injected to the tail vein of the mice 2 days before the injection of the melanoma cells into the tail vein.

As an angiotensin II receptor antagonist, used were valsartan (trade name: Diovan made by Novartis Pharma K.K.), losartan (trade name: Nu-Lotan made by MSD K.K.), olmesartan medoxomil (trade name: Olmetecmade by Daiichi Sankyo Co., Ltd.), azilsartan (trade name: Azilva made by Takeda Pharmaceutical Co., Ltd.), candesartan cilexetil (trade name: Blopress made by Takeda Pharmaceutical Co., Ltd.), and irbesartan (trade name: Avapro made by Sumitomo Dainippon Pharma Co., Ltd.).

To the angiotensin II receptor antagonist group, a 0.5% methylcellulose aqueous solution prepared so as to contain valsartan (40 mg/kg), losartan (30 mg/kg), olmesartan medoxomil (5 mg/kg), azilsartan (10 mg/kg), candesartan cilexetil (8 mg/kg), or irbesartan (100 mg/kg) was orally given for 4 days before the start of the experiment (before the injection of tumor cells to mice). After the injection of tumor cells, the oral intake of methylcellulose aqueous solutions containing telmisartan or pitavastatin in the above doses in the angiotensin II receptor antagonist group and the pitavastatin group was continued until the end of the experiment. To the control group, a 0.5% methylcellulose aqueous solution not containing any of the agents was orally given before the start of the experiment. The sample size of each group was n=5.

Figure 7:
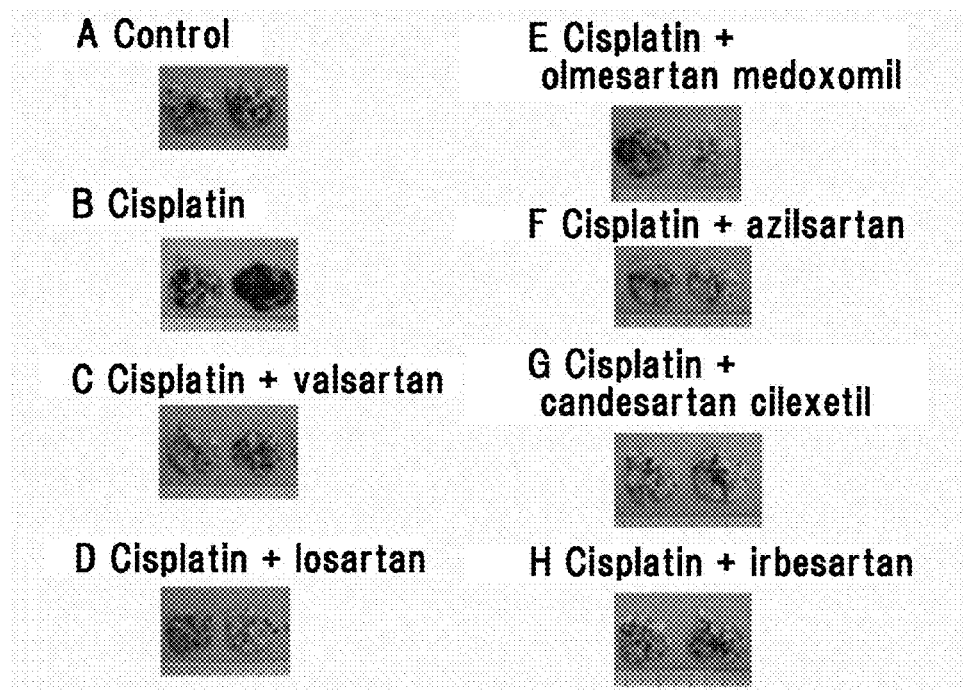
FIG. 7 shows micrographs of lungs at 14 days from the injection of mouse melanoma B16-F10 tumor cells into the tail vein of mice in a tail vein injection metastasis test where CDDP (5 mg/kg) was administered alone, or CDDP (5 mg/kg) was administered with valsartan, losartan, olmesartan medoxomil, azilsartan, candesartan cilexetil, or irbesartan (A: the lungs of a mouse as a control, B: the lungs of a mouse to which CDDP (5 mg/kg) was administered, C: the lungs of a mouse to which CDDP (5 mg/kg) and valsartan (40 mg/kg) were administered, D: the lungs of a mouse to which CDDP (5 mg/kg) and losartan (30 mg/kg) were administered, E: the lungs of a mouse to which CDDP (5 mg/kg) and olmesartan medoxomil (5 mg/kg) were administered, F: the lungs of a mouse to which CDDP (5 mg/kg) and azilsartan (10 mg/kg) were administered, G: the lungs of a mouse to which CDDP (5 mg/kg) and candesartan cilexetil (8 mg/kg) were administered, H: the lungs of a mouse to which CDDP (5 mg/kg) and irbesartan (100 mg/kg) were administered). Black parts are nodules (metastatic foci) formed by metastasized melanoma.
Figure 8:
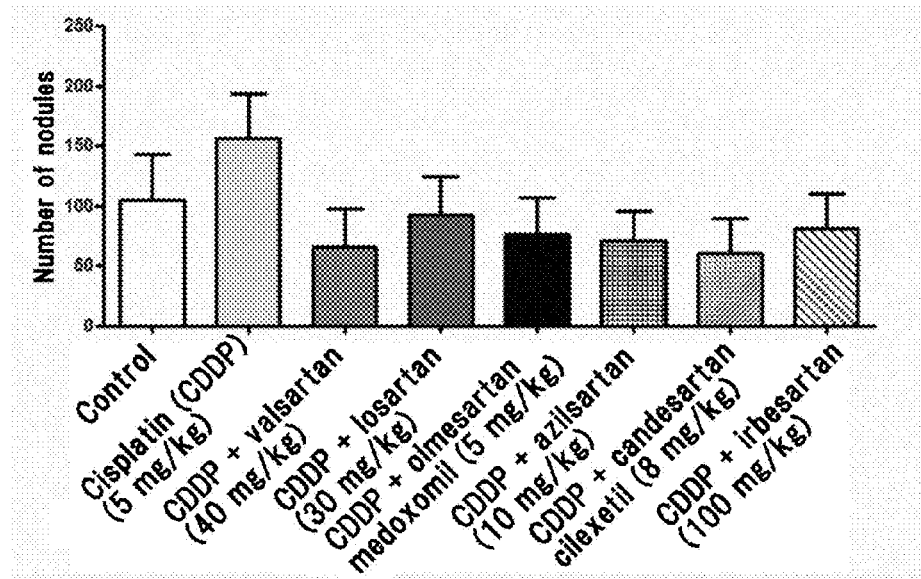
FIG. 8 shows a graph showing the number of nodules formed due to lung metastasis at 14 days from the injection of mouse melanoma B16-F10 tumor cells into the tail vein of mice in a tail vein injection metastasis test where CDDP (5 mg/kg) was administered alone, or CDDP (5 mg/kg) was administered with valsartan, losartan, olmesartan medoxomil, azilsartan, candesartan cilexetil, or irbesartan. The vertical axis indicates the number of nodules formed in the lungs per individual. Each bar is for, from the left to the right, the control group (physiological saline), the CDDP group (5 mg/kg), the group to which CDDP (5 mg/kg) and valsartan (40 mg/kg) were administered, the group to which CDDP (5 mg/kg) and losartan (30 mg/kg) were administered, the group to which CDDP (5 mg/kg) and olmesartan medoxomil (5 mg/kg) were administered, the group to which CDDP (5 mg/kg) and azilsartan (10 mg/kg) were administered, the group to which CDDP (5 mg/kg) and candesartan cilexetil (8 mg/kg) were administered, and the group to which CDDP (5 mg/kg) and irbesartan (100 mg/kg) were administered.

The condition of the lung metastasis of the tumor cells 2 weeks (14 days) after the tumor cell injection was observed. The results are shown in FIG. 7. FIG. 8 shows the number of observed nodules per animal formed due to lung metastasis (average and standard deviation of n=5).

FIGS. 7 and 8 show that the administration of cisplatin (CDDP) augmented tumor metastasis, but valsartan, losartan, olmesartan medoxomil, azilsartan, candesartan cilexetil, and irbesartan significantly suppressed the exacerbation of lung metastasis caused by CDDP.

Example 3

Vasoprotective Effect on Human Lung Arterial Microvascular Endothelial Cells

Figure 9:
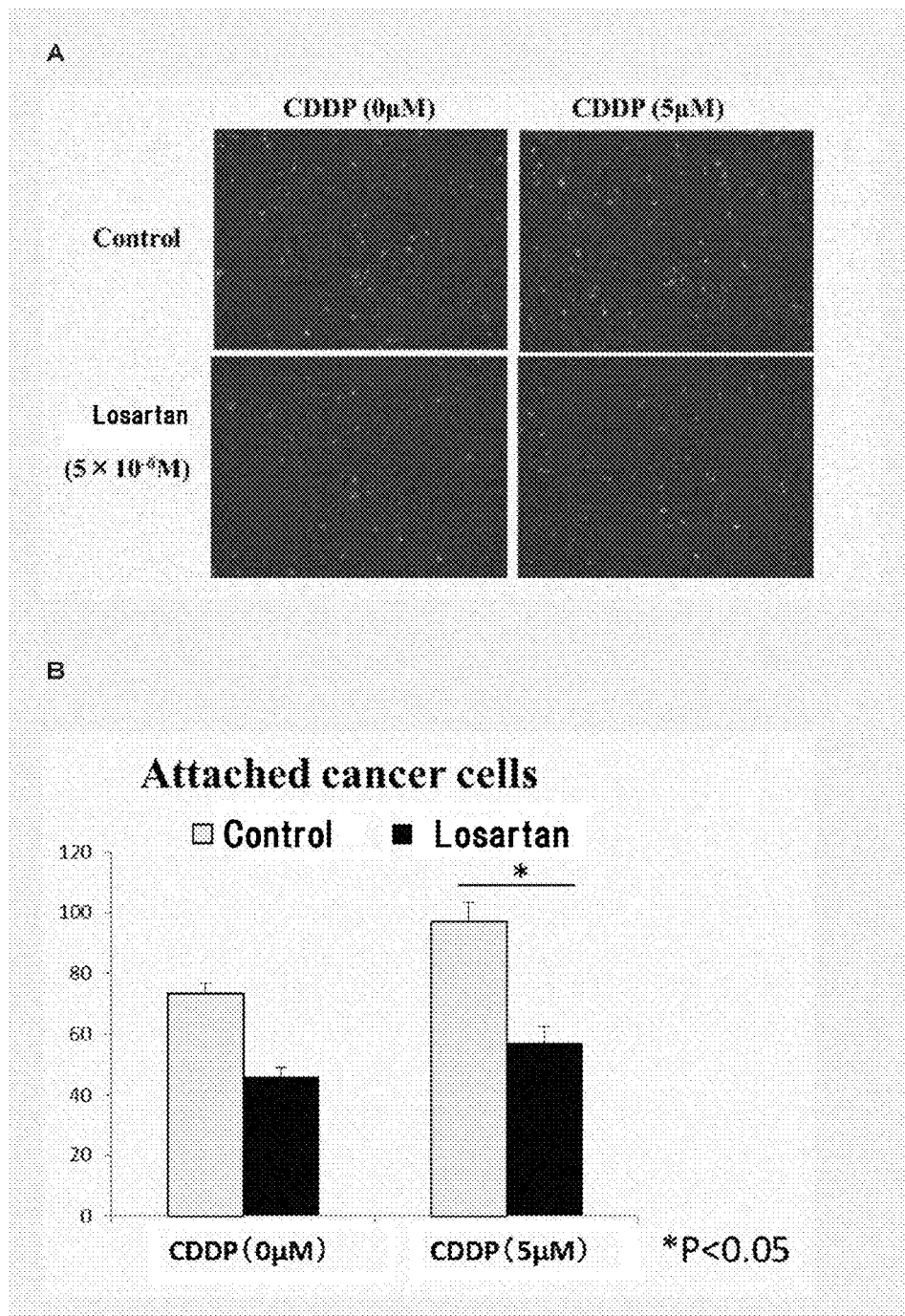
FIG. 9 shows the results of co-culture carried out as follows. Human lung arterial microvascular endothelial cells were cultured to confluence, losartan was added thereto (to a final concentration of $5\times10^{-6}$ M), and 2 hours later, phosphate buffered saline (PBS) or cisplatin (CDDP) was added (to a final concentration of 5 µM). An hour later, the culture medium was replaced with a fresh culture medium (Medium 199 containing 1% BSA). To this, a suspension of fluorescently-labeled A549 human lung cancer cells ($1\times10^5$ cells) was added, and the cells were co-cultured for 3 hours. After the co-culture, non-adherent cancer cells were washed out with cold PBS, and then 15-minute fixation with 4% formalin was performed.

Human lung arterial microvascular endothelial cells (manufactured by Lonza Japan) were cultured to confluence, losartan was added thereto (to a final concentration of $5 \times 10^{-6}$ M), and 2 hours later, phosphate buffered saline (PBS) or cisplatin (CDDP) was added (to a final concentration of 5 μM). An hour later, the culture medium was replaced with a fresh culture medium (Medium 199 (of Gibco brand manufactured by Invitrogen) containing 1% bovine serum albumin (BSA) manufactured by Sigma). To this, a suspension of fluorescently-labeled A549-GFP human lung cancer cells (manufactured by AntiCancer Japan) ($1 \times 10^5$ cells) was added, and the endothelial cells and lung cancer cells were co-cultured for 3 hours. As a result, the 1-hour pretreatment with 5 μM CDDP increased the number of cancer cells adhered to the vascular endothelial cells, but the pretreatment with losartan ($5 \times 10^{-6}$M) performed 2 hours before the CDDP pretreatment significantly suppressed the adhesion of cancer cells to the vascular endothelial cells. The results are shown in FIGS. 9A and 9B.

INDUSTRIAL APPLICABILITY

The present invention provides an excellent medicinal composition capable of suppressing the metastasis of a malignant tumor, a method for suppressing or preventing the metastasis, and a method for treating or preventing the metastasis of a malignant tumor. Further, the present invention exerts an excellent metastasis suppressing effect even on a malignant tumor of which the metastasis has been exacerbated by an anticancer and/or antitumor agent. Therefore, the present invention is useful in the fields of medicine etc.

---

The invention claimed is:

1. A method for suppressing the metastasis of a malignant tumor, the method comprising administering, to a patient, an effective amount of ghrelin or its derivative, where the ghrelin or its derivative is a peptide having an amino acid sequence represented by SEQ ID NO:1 or 2 in which the amino acid residue at the 3rd position from the amino terminus is a modified amino acid residue having a side chain acylated with n-octanoic acid, and having an agonistic effect on growth hormone secretagogue receptor 1a.

2. A method for suppressing exacerbation and/or augmentation of metastasis of a malignant tumor caused by an anticancer and/or antitumor agent, the method comprising administering, to a patient, an effective amount of ghrelin or its derivative, where the ghrelin or its derivative is a peptide having an amino acid sequence represented by SEQ ID NO:1 or 2 in which the amino acid residue at the 3rd position from the amino terminus is a modified amino acid residue having a side chain acrylated with n-octanoic acid, and having an agonistic effect on growth hormone secretagogue receptor 1a.

3. The method of claim 1, wherein the metastasis of the malignant tumor is metastasis to the lung, the bone, the liver, or the brain.

4. The method of claim 3, wherein the metastasis of the malignant tumor is metastasis to the lung or the liver.

5. The method of claim 1, wherein the malignant tumor is selected from the group consisting of epithelial malignant tumor, non-epithelial malignant tumor, and melanoma.

6. The method of claim 5, wherein the malignant tumor is melanoma.

7. The method of claim 1, wherein a subject of administration is a patient who is to undergo or who has undergone resection of a malignant tumor.

8. The method of claim 1, wherein a subject of administration is a patient who is receiving or who has received administration of an anticancer/antitumor agent.

9. The method of claim 1, which is for use in combination with an anticancer/antitumor agent.

10. The method of claim 9, wherein the anticancer/antitumor agent is a platinum-based antitumor agent.

* * * * *

SEQUENCE LISTING

```
<160> NUMBER OF SEQ ID NOS: 14

<210> SEQ ID NO 1
<211> LENGTH: 28
<212> TYPE: PRT
<213> ORGANISM: Homo sapiens
<220> FEATURE:
<221> NAME/KEY: PEPTIDE
<223> OTHER INFORMATION: Amino acid sequence for human ghrelin

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
<220> FEATURE:
<221> NAME/KEY: PEPTIDE
<223> OTHER INFORMATION: Amino acid sequence for human ghrelin

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25
```

<210> SEQ ID NO 3
<211> LENGTH: 28
<212> TYPE: PRT
<213> ORGANISM: Rattus norvegicus
<220> FEATURE:
<221> NAME/KEY: PEPTIDE
<223> OTHER INFORMATION: Amino acid sequence for rat ghrelin

<400> SEQUENCE: 3

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Rattus norvegicus
<220> FEATURE:
<221> NAME/KEY: PEPTIDE
<223> OTHER INFORMATION: Amiino acid sequence for rat ghrelin

<400> SEQUENCE: 4

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 5
<211> LENGTH: 28
<212> TYPE: PRT
<213> ORGANISM: Mus musculus
<220> FEATURE:
<221> NAME/KEY: PEPTIDE
<223> OTHER INFORMATION: Amino acid sequence for mouse ghrelin

<400> SEQUENCE: 5

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa
<220> FEATURE:
<221> NAME/KEY: PEPTIDE
<223> OTHER INFORMATION: Amino acid sequence for porcine ghrelin

<400> SEQUENCE: 6

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Bos taurus
<220> FEATURE:
<221> NAME/KEY: PEPTIDE
<223> OTHER INFORMATION: Amino acid sequence for bovine ghrelin

<400> SEQUENCE: 7

```
Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries
<220> FEATURE:
<221> NAME/KEY: PEPTIDE
<223> OTHER INFORMATION: Amino acid sequence for ovine ghrelin

<400> SEQUENCE: 8

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 9
<211> LENGTH: 28
<212> TYPE: PRT
<213> ORGANISM: Canis familiaris
<220> FEATURE:
<221> NAME/KEY: PEPTIDE
<223> OTHER INFORMATION: Amino acid sequence for dog ghrelin

<400> SEQUENCE: 9

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Equus caballus
<220> FEATURE:
<221> NAME/KEY: PEPTIDE
<223> OTHER INFORMATION: Amino acid sequence for equine ghrelin

<400> SEQUENCE: 10

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25

<210> SEQ ID NO 11
<211> LENGTH: 1457
<212> TYPE: DNA
<213> ORGANISM: Homo sapiens
<220> FEATURE:
<221> NAME/KEY: CDS
<222> LOCATION: (165)..(722)

<400> SEQUENCE: 11
ggcacgagct ggatagaaca gctcaagcct tgccacttcg ggcttctcac tgcagctggg      60
cttggacttc ggagttttgc cattgccagt gggacgtctg agactttctc cttcaagtac    120
ttggcagatc actctcttag cagggtctgc gcttcgcagc cggg atg aag ctg gtt    176
                                                 Met Lys Leu Val
                                                  1 tcc gtc gcc ctg atg tac ctg ggt tcg ctc gcc ttc cta ggc gct gac    224
Ser Val Ala Leu Met Tyr Leu Gly Ser Leu Ala Phe Leu Gly Ala Asp
    5                   10                  15                  20
```

| | |
|---|---|
| acc gct cgg ttg gat gtc gcg tcg gag ttt cga aag aag tgg aat aag<br>Thr Ala Arg Leu Asp Val Ala Ser Glu Phe Arg Lys Lys Trp Asn Lys<br>                     25                     30                  35 | 272 |
| tgg gct ctg agt cgt ggg aag agg gaa ctg cgg atg tcc agc agc tac<br>Trp Ala Leu Ser Arg Gly Lys Arg Glu Leu Arg Met Ser Ser Ser Tyr<br>                40                     45                  50 | 320 |
| ccc acc ggg ctc gct gac gtg aag gcc ggg cct gcc cag acc ctt att<br>Pro Thr Gly Leu Ala Asp Val Lys Ala Gly Pro Ala Gln Thr Leu Ile<br>             55                     60                     65 | 368 |
| cgg ccc cag gac atg aag ggt gcc tct cga agc ccc gaa gac agc agt<br>Arg Pro Gln Asp Met Lys Gly Ala Ser Arg Ser Pro Glu Asp Ser Ser<br> 70                     75                     80 | 416 |
| ccg gat gcc gcc cgc atc cga gtc aag cgc tac cgc cag agc atg aac<br>Pro Asp Ala Ala Arg Ile Arg Val Lys Arg Tyr Arg Gln Ser Met Asn<br>85                     90                     95               100 | 464 |
| aac ttc cag ggc ctc cgg agc ttt ggc tgc cgc ttc ggg acg tgc acg<br>Asn Phe Gln Gly Leu Arg Ser Phe Gly Cys Arg Phe Gly Thr Cys Thr<br>               105                  110                115 | 512 |
| gtg cag aag ctg gca cac cag atc tac cag ttc aca gat aag gac aag<br>Val Gln Lys Leu Ala His Gln Ile Tyr Gln Phe Thr Asp Lys Asp Lys<br>            120                  125                130 | 560 |
| gac aac gtc gcc ccc agg agc aag atc agc ccc cag ggc tac ggc cgc<br>Asp Asn Val Ala Pro Arg Ser Lys Ile Ser Pro Gln Gly Tyr Gly Arg<br>               135                  140                145 | 608 |
| cgg cgc cgg cgc tcc ctg ccc gag gcc ggc ccg ggt cgg act ctg gtg<br>Arg Arg Arg Arg Ser Leu Pro Glu Ala Gly Pro Gly Arg Thr Leu Val<br>            150                  155                160 | 656 |
| tct tct aag cca caa gca cac ggg gct cca gcc ccc ccg agt gga agt<br>Ser Ser Lys Pro Gln Ala His Gly Ala Pro Ala Pro Pro Ser Gly Ser<br>165                   170                  175               180 | 704 |
| gct ccc cac ttt ctt tag gatttaggcg cccatggtac aaggaatagt<br>Ala Pro His Phe Leu<br>               185 | 752 |
| cgcgcaagca tcccgctggt gcctcccggg acgaaggact tcccgagcgg tgtggggacc | 812 |
| gggctctgac agccctgcgg agaccctgag tccgggaggc accgtccggc ggcgagctct | 872 |
| ggctttgcaa gggcccctcc ttctgggggc ttcgcttcct tagccttgct caggtgcaag | 932 |
| tgccccaggg ggcggggtgc agaagaatcc gagtgtttgc caggcttaag gagaggagaa | 992 |
| actgagaaat gaatgctgag accccggag cagggggtctg agccacagcc gtgctcgccc | 1052 |
| acaaactgat ttctcacggc gtgtcacccc accagggcgc aagcctcact attacttgaa | 1112 |
| ctttccaaaa cctaaagagg aaaagtgcaa tgcgtgttgt acatacagag gtaactatca | 1172 |
| atatttaagt ttgttgctgt caagattttt tttgtaactt caaatataga gatattttttg | 1232 |
| tacgttatat attgtattaa gggcatttta aaagcaatta tattgtcctc ccctattta | 1292 |
| agacgtgaat gtctcagcga ggtgtaaagt tgttcgccgc gtggaatgtg agtgtgtttg | 1352 |
| tgtgcatgaa agagaaagac tgattacctc ctgtgtggaa gaggaaaaca ccgagtctct | 1412 |
| gtataatcta tttacataaa atgggtgata tgcgaacagc aaacc | 1457 |

<210> SEQ ID NO 12
<211> LENGTH: 185
<212> TYPE: PRT
<213> ORGANISM: Homo sapiens

<400> SEQUENCE: 12

Met Lys Leu Val Ser Val Ala Leu Met Tyr Leu Gly Ser Leu Ala Phe
1                 5                   10                   15

```
Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
                35                  40                  45

Ser Ser Ser Tyr Pro Thr Gly Leu Ala Asp Val Lys Ala Gly Pro Ala
 50                              55                  60

Gln Thr Leu Ile Arg Pro Gln Asp Met Lys Gly Ala Ser Arg Ser Pro
 65                      70                  75                  80

Glu Asp Ser Ser Pro Asp Ala Ala Arg Ile Arg Val Lys Arg Tyr Arg
                 85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
130                 135                     140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 13
<211> LENGTH: 52
<212> TYPE: PRT
<213> ORGANISM: Homo sapiens

<400> SEQUENCE: 13

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
 50

<210> SEQ ID NO 14
<211> LENGTH: 20
<212> TYPE: PRT
<213> ORGANISM: Homo sapiens

<400> SEQUENCE: 14

Ala Arg Leu Asp Val Ala Ser Glu Phe Arg Lys Lys Trp Asn Lys Trp
 1               5                  10                  15

Ala Leu Ser Arg
            20
```